United States Patent
Sun

(10) Patent No.: US 8,519,726 B2
(45) Date of Patent: Aug. 27, 2013

(54) SENSOR HAVING INTEGRATED ELECTRODES AND METHOD FOR DETECTING ANALYTES IN FLUIDS

(76) Inventor: Yizhong Sun, Castaic, CA (US)

( * ) Notice: Subject to any disclaimer, the term of this patent is extended or adjusted under 35 U.S.C. 154(b) by 736 days.

(21) Appl. No.: 12/661,794

(22) Filed: Mar. 24, 2010

(65) Prior Publication Data
US 2010/0188110 A1    Jul. 29, 2010

Related U.S. Application Data

(63) Continuation-in-part of application No. 12/217,644, filed on Jul. 8, 2008, now Pat. No. 7,812,622, which is a continuation of application No. 10/238,794, filed on Sep. 9, 2002, now Pat. No. 7,465,425.

(51) Int. Cl.
  *G01R 27/08* (2006.01)
  *G01R 27/26* (2006.01)
  *G01R 27/02* (2006.01)

(52) U.S. Cl.
  USPC ........... 324/707; 324/439; 324/674; 324/681; 324/686

(58) Field of Classification Search
  USPC .................. 324/684, 707, 439, 674, 681, 686
  See application file for complete search history.

(56) References Cited

U.S. PATENT DOCUMENTS

| | | | |
|---|---|---|---|
| 4,733,556 A * | 3/1988 | Meitzler et al. | 73/53.05 |
| 4,887,455 A | 12/1989 | Payne et al. | |
| 5,571,401 A | 11/1996 | Lewis et al. | |
| 6,175,752 B1 * | 1/2001 | Say et al. | 600/345 |
| 6,319,724 B1 | 11/2001 | Lewis et al. | |
| 6,631,333 B1 | 10/2003 | Lewis et al. | |
| 7,465,425 B1 | 12/2008 | Sun | |
| 2009/0261987 A1 | 10/2009 | Sun | |

OTHER PUBLICATIONS

U.S. Appl. No. 12/154,301, Sun, Y.
U.S. Appl. No. 12/217,644, Sun, Y.

* cited by examiner

*Primary Examiner* — Arleen M Vazquez
*Assistant Examiner* — Son Le

(57) ABSTRACT

A sensor having integrated electrodes in a single sensor configuration, which is operated by alternating current (AC) including periodic electrical excitation signals of the respective multiple frequencies with the same amplitude for detecting analytes in fluids. The sensor applies a total of an odd number of the identical conductors serving as the respective electrodes, which are positioned equally spaced apart, in order, alignment and parallel with each other. The odd numbered conductors of the total conductors are connected in parallel by a first electrically conducting means serving as a first electrical pole to form a first group of the integrated electrodes. The even numbered conductors are connected in parallel by a second electrically conducting means serving as a second electrical pole to form a second group of the integrated electrodes. The present invention sensor possesses properties of high output, reduced physical size and improved electrical characteristics.

20 Claims, 6 Drawing Sheets

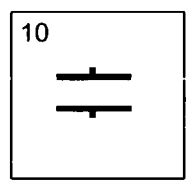
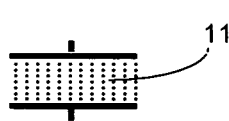
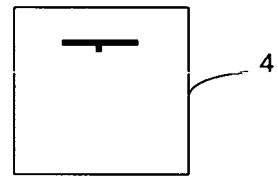
FIG. 4  FIG. 6  FIG. 7A
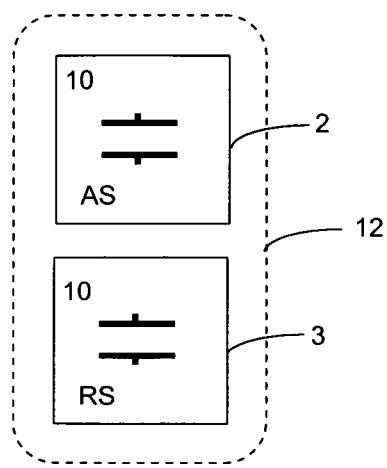
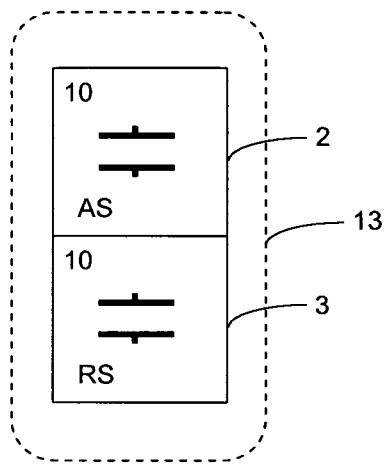
FIG. 4A  FIG. 4B
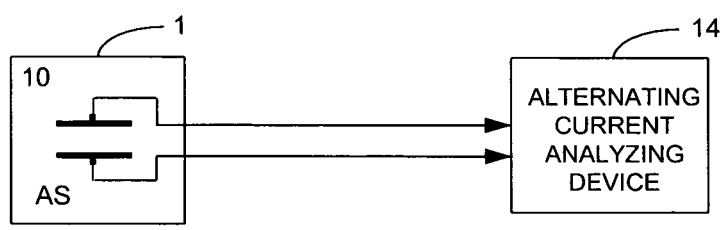
FIG. 5

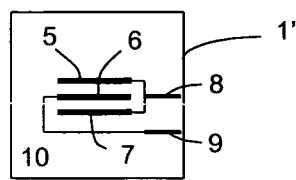
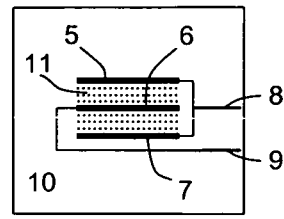
FIG. 8  FIG. 10
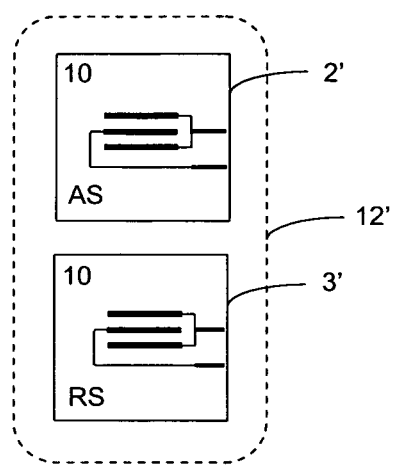
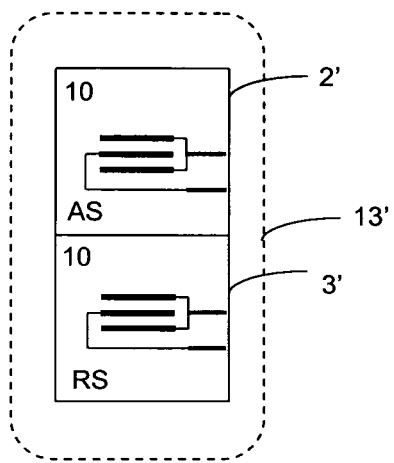
FIG. 8A  FIG. 8B
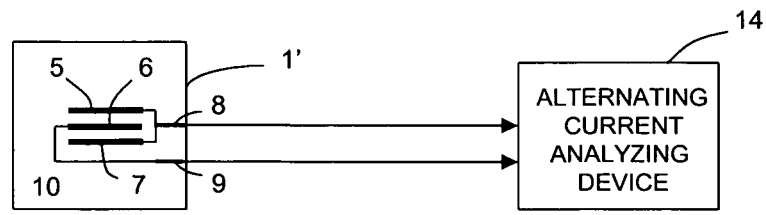
FIG. 9

SENSOR HAVING INTEGRATED ELECTRODES AND METHOD FOR DETECTING ANALYTES IN FLUIDS

CROSS-REFERENCE TO RELATED APPLICATION

This application is a continuation-in-part of application Ser. No. 12/217,644 filed on Jul. 8, 2008, now U.S. Pat. No. 7,812,622, that is a continuation of application Ser. No. 10/238,794, now U.S. Pat. No. 7,465,425.

BACKGROUND OF THE INVENTION

1. Field of the Invention

The present invention relates generally to the field of sensors, and more particularly relates to sensors including methods for detecting analytes in fluids.

2. Description of the Prior Art

Sensors are widely used in the technology of detecting analytes present in fluids. The following references are pertinent to this field of art:
1. U.S. Pat. No. 4,887,455 issued on Dec. 19, 1989 to Payne et al. for "Gas Sensor" (hereafter "the '455 Payne patent");
2. U.S. Pat. No. 5,571,401 issued on Nov. 5, 1996 to Lewis et al. for "Sensor Arrays for Detecting Analytes in Fluids" (hereafter "the '401 Lewis patent");
3. U.S. Pat. No. 6,319,724 issued on Nov. 20, 2001 to Lewis et al. for "Trace Level Detection of Analytes Using Artificial Olfactometry" (hereafter "the '724 Lewis patent");
4. Payne, et al., "High-Frequency Measurements of Conducting Polymers: Development of A New Technique for Sensing Volatile Chemicals", Meas. Sci. Technol. 6 (1995) pp. 1500-1507 (hereafter "the Payne Publication");
5. Nagle, H. T., et al., "The How And Why Of Electronic Nose", IEEE Spectrum, September 1998, pp. 22-34 (hereafter "the Nagle Publication");
6. Baltes, H., et al., "The Electronic Nose In Lilliput", IEEE Spectrum, September 1998, pp. 35-38 (hereafter "the Baltes Publication");
7. U.S. Pat. No. 6,631,333 issued on Oct. 7, 2003 to Lewis et al. for "Methods For Remote Characterization Of An Odor" (hereafter "the '333 Lewis patent", in addition to U.S. Pat. No. 7,359,802 issued on Apr. 15, 2008 to the same inventors, which is a Divisional patent of the '333 Lewis patent);
8. U.S. Pat. No. 7,465,425 issued on Dec. 16, 2008 to Sun for "Sensor And Method For Detecting Analytes In Fluids" (hereafter "the '425 Sun patent"); and
9. U.S. Pat. No. 7,696,363 issued on Apr. 13, 2010 to Sun for "Sensor And Method For Detecting Analytes In Fluids" (hereafter "the '763 Sun patent").

The '455 Payne patent discloses a gas sensor that has a semiconductive organic polymer layer exposed to a gas to be detected. An analyzer applies an alternating electric signal at specific resonant frequencies to the sensor for detecting the change in the sensor's impedance characteristics which is compared by a microcomputer with reference characteristics stored in a memory of the microcomputer. The gas in contact with the sensor can be detected because of the resulting difference spectra of its impedance characteristics. The patent further discloses that the best performance of the invention is likely to be conducted with frequencies ranging 100 MHZ to 500 MHZ where the resonance may happen.

The '401 Lewis patent discloses arrays of chemical sensors, including polymer carbon powder based chemiresistors for detecting analytes in fluids. The sensor include first and second conductive elements electrically coupled to and separated by a chemically sensitive resistor which provides an electrical path between the conductive elements. The resistor includes a plurality of alternating nonconductive regions made of a nonconductive organic polymer and conductive regions made of a conductive material transverse to the electrical path. The resistor further provides a difference in resistance between the conductive elements when contacted with a fluid containing a chemical analyte at a first concentration, and then at a second different concentration. Arrays of such sensors are constructed with at least two sensors having different chemically sensitive resistors providing differences in resistance. Variability in chemical sensitivity from sensor to sensor is provided by qualitatively or quantitatively varying the composition of the conductive and/or nonconductive regions. An "electronic nose" for detecting an analyte in a fluid may be constructed by using such arrays in conjunction with an electrical measuring device electrically connected to the conductive elements of each sensor.

The '401 Lewis patent discloses arrays of chemical sensors, including polymer carbon powder based chemiresistor for detecting analytes in fluids. The sensors include first and second conductive elements electrically coupled to and separated by a chemically sensitive resistor which provides an electrical path between the conductive elements. The resistor includes a plurality of alternating nonconductive regions made of a nonconductive organic polymer and conductive regions made of a conductive material transverse to the electrical path. The resistor further provides a difference in resistance between the conductive elements when contacted with a fluid containing a chemical analyte at a first concentration, and then at a second different concentration. Arrays of such sensors are constructed with at least two sensors having different chemically sensitive resistors providing differences in resistance. Variability in chemical sensitivity from sensor to sensor is provided by qualitatively or quantitatively varying the composition of the conductive and/or nonconductive regions. An "electronic nose" for detecting an analyte in a fluid may be constructed by using such arrays in conjunction with an electrical measuring device electrically connected to the conductive elements of each sensor.

The '724 Lewis patent discloses a method using artificial olfactometry for detecting the presence of an analyte indicative of various medical conditions, including halitosis, periodontal disease and other diseases.

The Payne Publication discloses the change in the alternating current (AC) impedance characteristics of poly-N-(2-pyridyl) pyrrole in the presence of different volatile chemicals.

The Nagle Publication is a special report, which summarizes research and development of the electronic nose instrument through 1990's. The report in detail introduces types of sensors including the respective sensing mechanisms for metal oxide thin film resistor sensors, conductive polymer sensors, polymer coated quartz crystal microbalance (QCM) sensors, polymer coated surface acoustic wave (SAW) sensors, metal-oxide-silicon field-effect-transistor (MOSFET) sensors, dye coated optical fiber (DCOF) sensors, gas chromatography (GC), light spectrum, and mass spectrometry (MS). The report also discloses advantages and disadvantages according to the respective sensors including the sensing mechanisms, wherein a high sensitivity to humidity is addressed as the disadvantage of the polymer film based sensors.

The Baltes Publication reports the developed micronose integrated circuit sensor CMOS chip coated with polymer films according to mechanisms of sensing mass change and dielectric constant change of the polymer films when they load up on volatile organic compounds.

The '333 Lewis patent discloses compositions and systems useful in remote monitoring of chemical hazards, air quality and medical conditions. For example, robotic systems search for and detect explosives, mines, and hazardous chemicals. In addition, the methods, systems and compositions of the invention provide the ability to mine data from database containing a plurality of chemical fingerprints. The patent also summarizes techniques for constructing sensors as disclosed in the Nagle Publication, in addition to a dye-impregnated bread (DIB) arrays and micromachined cantilever (MMC) arrays. The patent further discloses the invented electrically conductive sensor that comprises alternating regions of a conductive material and a material compositionally different than the conductive material between two conductive leads wherein said sensor provides an electrical path through the regions of conductive material and the regions of the compositionally different material.

It can be seen from the above cited references that significant efforts have been devoted in the past for researching and developing configuration of sensors. This is because the configuration of the sensors predominantly governs sensor performance for detecting and identifying analytes in fluids. Specifically, identification of analytes in fluids is accomplished through applying sensors which mimic mechanisms of the mammalian olfactory system that applies probabilistic repertoires of many different receptors to record a single odorant. Having such sensor technologies in conjunction with existing technologies in electrical engineering including highly integrated circuit chips (ICs), advanced softwares, the current sensor technologies improve convenience in detection and identification of analytes.

It is well known that, from studying the mammalian olfactory system, identification of the odorant is dependent upon not only the results from highly specific receptors but also the output from less specific ones. In other words, identification is based on recognizing a spectrum of signals that resemble a specific pattern. Following this direction, conventional technologies in sensor configuration are developed according to the following two schemes to generate a signal spectrum: applying strategies of a multiple sensor configuration and a single sensor configuration.

In the approaches that utilize the multiple sensor configuration, which are disclosed by the Nagle Publication in addition to the '333 Lewis patent, various detecting devices have been developed that use metal oxide thin film resistor sensors, conductive polymer or polymer carbon powder composite film chemi-resistor sensors, QCM, SAW, MOSFET and DCOF sensors, and DIB and MMC arrays. However, although much progress has been made in the past, there are still primary disadvantages inherited from the sensing mechanisms of such multiple sensor technologies. The disadvantages include the requirement of a large number of sensors to generate a patterned information, the sophistication of the sensor configuration, thus the resulting poor reproducibility in sensor manufacturing, the strong humidity influence applying polymer film modified sensors on chemical analysis, the slow response, the expensive electronic equipment required, and the very restricted operating conditions.

In the approaches that utilize the multiple sensor configuration, which are disclosed by the Nagle Publication in addition to the 333 Lewis patent, various detecting devices have been developed that use metal oxide thin film resistor sensors, conductive polymer or polymer carbon powder composite film chemi-resistor sensors, QCM, SAW, MOSFET and DCOF sensors, and DIB and MMC arrays. However, although much progress has been made in the past, there are still primary disadvantages inherited from the sensing mechanisms of such multiple sensor technologies. The disadvantages include the requirement of a large number of sensors to generate a patterned information, the sophistication of the sensor configuration, thus the resulting poor reproducibility in sensor manufacturing, the strong humidity influence applying polymer film modified sensors on chemical analysis, the slow response, the expensive electronic equipment required, and the very restricted operating conditions.

Various polymer films with a general thickness of several micrometers have been extensively used in the multiple sensor configuration to improve sensor sensitivity and detection limit. This is primarily due to the fact that the polymer films can trap including adsorb and absorb analytes of the respective chemicals, according to their specific chemical selectivities on the analytes. As a result, the analytes will be concentrated on the surface or inside of the polymer films prior to detection.

However, the conventional polymer films also inherit a number of disadvantages. First, the thin films of polymer are sensitive to the humidity associated with analytes. Humidity is the predominant factor to influence performance of the polymer film based gas sensors. Second, polymer films have an aging effect that affects the sensor stability for long term usages. Third, it is difficult to achieve reproducibility of the polymer films used in sensors, particularly in a situation when a large number of the sensors must be used in the multiple sensor configuration.

In the approaches for a single sensor configuration also disclosed by the Nagle Publication, various instruments have been developed that are based on the mechanisms of GC, MS, and light spectrum. Generally, these instruments are very expensive. Moreover, they are typically very bulky in size, which makes their miniaturization almost impossible. As a result, they are less attractive in the market, where portability of the instruments becomes increasingly important.

For example, a strategy of point-of-care (POC) is becoming an urgent demand in the field of medical diagnoses. Under the strategy POC, patient healthcare including medical diagnoses are directly conducted at the patients' bedsides of the respective patients' homes. Therefore, medical instruments are advantageous if they are completely portable. In fact, instruments having portabilities are critical in many fields besides the medical field, including security, military and industrial fields.

As an example utilizing the single sensor configuration, the Payne Patent and Payne Publication cited above disclose application of a single sensor for detecting the presence of gaseous analytes from detecting impedance and phase sensitive components of conductive polymer modified electrodes at specific frequencies, where electrical resonant signals are established due to interaction of analytes to the conductive polymer film. However, the Payne device requires high frequencies ranging from 100 MHz to 500 MHz, where the resonance may occur. The high frequency brings significant difficulties in sensor manufacturing and application. In addition, it still has the disadvantages inherent from polymer films.

As an example utilizing the single sensor strategy, the Payne patent and Payne Publication cited above disclose application of a single sensor for detecting the presence of gaseous analytes from detecting impedance and phase sensitive components of conductive polymer modified electrodes at specific frequencies, where electrical resonant signals are established due to interaction of analytes to the conductive polymer film. However, the Payne device requires high frequencies ranging from 100 MHz to 500 MHz, where the resonance may occur. The high frequency brings significant difficulties in sensor manufacturing and application. In addition, it still has the disadvantages inherent from polymer films.

In order to overcome deficiencies of the Payne technologies and invent a new sensor in the single sensor configuration with applying multiple frequency technology and vector analysis, the '425 Sun patent discloses a sensor serving as an analytical sensor for detecting and identifying analytes in fluids. The sensor is constructed from applying a pair of electrodes, wherein between the electrodes there are no additional materials designated to adsorb analytes if their concentrations are high, or there are adsorbents if the analyte concentrations are low. An alternating current voltage of varying frequencies is applied to the sensor by an alternating current device. In return, it detects electrical properties such as impedance and its components, reactance, resistance, and phase angles of the sensor with a subject of an analyte in a fluid when the subject resides in or passes through the electrodes at each frequency. Thus two spectra of electrical properties of the analyte can be established at various applied frequencies from a single measurement. The electrical properties are analyzed by a pattern recognition process, and compared with those of the known objects. Therefore, the analyte can be detected and identified. A reference sensor is provided with the same configuration of the analytical sensor. By combining electrical properties from the analytical and reference sensors, the '425 Sun patent provides a number of advantages, including selective detection of analytes of interest, and elimination of background effect including humidity influence, polymer film aging effect, and electrical property variations caused by the temperature variations.

The '763 Sun patent discloses various methods according to the disclosure of the '425 Sun patent, including for identifying analytes in fluids, detecting analytes in chromatography, and detecting hydrogen gases.

It will be appreciated that although the '425 and '763 Sun patents successfully disclose the sensor technology having two spaced apart electrodes in the single sensor configuration, there is stall a room for improving the sensor regarding its electrical characteristics, and output that is fundamental of the detection technology. This is because the output of the sensor is limited by the only one available gap between two electrodes, which are electrically polarized according to the alternative electrical polarities of the applied AC excitation. Therefore, the two electrodes alternatively having the different electrical polarities are exposed to an electrical environment that surrounds the sensor, so that there is a great chance for a cross talk between the sensor and surrounding electrical environment if the sensor is not electrically shielded.

Therefore, the present invention desires to develop a sensor including method that overcomes the disadvantages of conventional sensors, and has a better reproducibility of performance and sensor manufacturing, fewer interference deficiencies, enhanced sensitivities, less restricted operation conditions, increased portabilities, improved output and electrical, characteristics.

SUMMARY OF THE INVENTION

The present invention is aimed to invent a sensor having integrated electrodes in a single sensor configuration, which is operated by alternating current (AC) including periodic electrical excitation signals of the respective multiple frequencies with the same amplitude for detecting analytes in fluids. For a general embodiment of the integrated electrodes, the sensor applies a total of an odd number of the identical conductors serving as the respective electrodes, which are positioned equally spaced apart, in order, alignment and parallel with each other. The even numbered conductors of the total conductors are connected in parallel by a first electrically conducting means serving as a first electrical pole to form a first group of the integrated electrodes. The odd numbered conductors are connected in parallel by a second electrically conducting means serving as a second electrical pole to form a second group of the integrated electrodes. The present invention sensor possesses properties of high output, reduced physical size and improved electrical characteristics.

In a preferred embodiment when it is in a simplest form, the sensor has identical first, second and third conductors serving as the respective electrodes which are positioned equally spaced apart, in order, alignment and parallel with each other. The first and third electrodes are the outer electrodes, and connected in parallel by a first electrically conducting means serving as a first electrical pole to thereby form a group of the integrated electrodes. The second electrode is the middle electrode, and connected by a second electrically conducting means which is served as a second electrical pole.

The present invention sensor is operated by multiple frequencies of AC excitation at the same amplitude from a single measurement, which obtains two sets of patterned AC electrical properties of an analyte according to the various frequencies having a preferred range from 10 KHz to 1 MHz. The electrical properties that are obtained at each frequency are governed by the natural characteristics of the analyte including the dielectric constant, polarity or dipole moment. Therefore, the analytes can be identified by comparing patterns of the respectively obtained AC electrical properties of the analytes with patterns of AC electrical properties of known chemicals of interest.

The present invention sensor and method also provides a dual sensor which includes two identical sensors, wherein one sensor is served as an analytical sensor and the other as a reference sensor. The analytical and reference sensors are operated by multiple frequencies of AC excitation at the same amplitude for measuring the respective sample of an analyte in a fluid and the same fluid but without any analyte. When combing output of the respective analytical and reference sensors, the present invention dual sensor can reduce influence of the background noises including humidity level, polymer film aging effect and electrical property variations caused by temperature variations of the analytical sensor. In addition, the present invention can selectively detect known chemical or chemicals serving as the respective biochemical marker or markers from the respective analytes for the medical diagnoses.

The present invention sensor and method further applies a temperature programming including the gradient and constant temperature programming on regulating temperature of the respective analytical and reference sensors having the respective analytes in fluids and same fluids without any analytes to improve performance of the analyte detection.

The present invention sensor and method has capabilities to apply all types of organic, inorganic, and metal adsorbent materials, which are positioned into the respective sensors to adsorb or absorb the respective analytes for improving detection of the analytes.

The present invention sensor and method provides a new and unique sensor in the single sensor configuration, which is compact in size, portable, easy to use, has less background influence, is inexpensive to produce, and is low in power consumption for controlling temperature of the sensor including the respective positioned analytes and fluids.

The present invention sensor and method also comprises an option having at least two sensors in the single sensor configuration, wherein each sensor is operated by various frequencies of AC excitation at the same amplitude for detecting analytes in fluids, which is electrically shielded for preventing cross-talk influence caused by electromagnetic radiation of the applied multiple including swept electrical frequencies. In addition, each of the at least two sensor is filled with different materials to adsorb and absorb the respective analytes.

The present invention provides the novel and unique sensor and method for identifying analytes in fluids. The identification of the analytes is based on detecting various patterned AC electrical properties of the respective analytes in fluids such as current, voltage and impedance including its components: resistance, reactance and phase angle, as they are governed by the analyte chemical characteristics. For the preferred embodiment, the three identical electrodes can have the respective air, ceramic and silicon substrates to thereby form the respective spatial, thick film and thin film electrodes, which are used to measure AC related electrical properties of the respective analytes residing or passing between the electrodes at varied including swept electrical frequencies comprising the preferred frequencies ranging from 10 KHz to 1 MHZ.

The measurement results in two sets of patterned AC electrical properties for each of the analytes at the applied varied including swept frequencies. Applying a pattern recognition procedure, patterns of the AC electrical properties of the respective analytes can be recognized. Therefore, the analytes can be identified by comparing the respective recognized patterns with patterns of the electrical properties of known analytes of interest.

As discussed, the identification of analytes in fluids from the present invention is based on generating various patterned AC electrical properties gathered from the respective analytes being tested, which properties are specific to the respective analytes and are gathered from various dimensions. Therefore, the present invention is focused on finding such specific electrical properties that are related to the natural characteristics of the respective analytes, which can be measured simultaneously by a technique.

For example, the dielectric constant is one of the natural characteristics of a chemical being the analyte of interest, which is in one dimension to describe the analyte. Thus the dielectric constant can be used to identify the analyte. The dielectric constant can be measured in the AC electricity as the capacitive reactance, which is a predominant part of the reactance for short electrodes. Therefore, the reactance is a good approximation for the capacitive reactance, wherein the reactance can be measured from an impedance complex in the vector domain. Hence, the reactance is one of the specific AC electrical properties of the analyte, and is also in one dimension useful for detecting and identifying the analyte from the present invention (in the scalar domain, capacitance is proportional to the dielectric constant and has been used for identifying chemicals, see the Balters Publication). Therefore, analytes can be detected and identified according to values of the reactance of the respective analytes.

In addition, regarding an analyte being a gaseous mixture, the dielectric constant of mixed gases can be estimated according to several methods. For example, the dielectric constant of the natural gas mixture is calculated as a function of temperature, density and composition of the mixture (Harvey, A. H.; Lemmon, E. W.; Method For Estimating The Dielectric Constant of Natural Gas Mixtures, *International Journal of Thermophysics*, Vol. 26, No. 1, 31-46, January 2005). The authors state that their method is better than the traditional mixing rule. Regarding an analyte being a liquid mixture, the dielectric constant of mixed liquid can be measured, which can be further explained according to the Clausius Mosotti theory, or the Onsager theory (Sen, A. D.; Anicich, V. G.; Arakelian; T; Dielectric Constant of Liquid Alkanes And Hydrocarbon Mixtures, *J. Phys. D: Appl. Phys.* 25 516-521).

It will be appreciated, from the above listed research, the dielectric constants still are served as the characteristics of the respective gaseous and liquid chemical mixtures. Therefore, the present invention can use the reactance to detect and identify the respective analytes of the chemical mixture in the respective gas and liquid phases.

Besides its dielectric constant, the chemical of an analyte has its unique composition of chemical elements possessing the respective characteristic electronegativities to thereby form the specific molecular dipole moment or polarity, which is another natural characteristics of the chemical. Such characteristics may be measured by resistance. For example, volatile organic chemicals including those rich in hydrogen and oxygen change electrical conductivity (resistivity) of metal oxide based sensors (see the Nagle and Balter Publications), wherein hydrogen and oxygen have the respective large electronegativities.

It will be appreciated that, the resistance in the AC electricity can also be simultaneously measured as another component of the impedance complex. The resistance compares with the measured reactance that is predominant in the impedance complex since an analyte in pure form (including the gas phase) is not electrically conductive. However, although the resistance is minor, it reflects resistive characteristics of the analyte and describes the analyte in another dimension of the chemical natural characteristics, which is further orthogonal to the dimension of the reactance. Therefore, the resistance information is also equally important for identifying the analyte.

With varying the frequencies in a single measurement, the present invention enables to obtain two sets of the patterned AC electrical properties such as resistance and reactance for an analyte, so as to the respective analytes for detection and identification purposes.

Impedance that is the summation of resistance and reactance including the capacitive reactance can be obtained applying Ohm's law in AC electricity:

$$Z=V/I \quad [1]$$

where Z is the impedance vector, V is the voltage vector, and I is the current vector. It can be understood that from the above equation, the voltage across the sensor is proportional to the impedance under a constant current technique. Current passing through the sensor electrodes is reversely proportional to the impedance applying a constant voltage technology. Therefore, as alternatives, either current or voltage can be used (in place of impedance) for detection and identification purpose.

The present invention sensor and method does not require additional materials positioned between the sensor electrodes for adsorbing analytes with sufficient concentrations. When the analyte concentrations are insufficient, the present invention has the option of using adsorbent materials in the sensor design to selectively adsorb or absorb analytes for improving sensitivities and detection limits of the sensor.

Obviously, the dimensions of the respective electrical properties including resistance and reactance from the sensor filled with adsorbent materials are different from those of the electrical properties of the sensor without having the materials. It is because the sensor filled with the adsorbent materials will record the AC electrical properties of a particular chemical or chemicals of an analyte in a fluid, wherein the chemical or chemicals are adsorbed by the adsorbent materials due to specific interactions among the chemical or chemicals and materials.

Therefore, having the spirit and scope of finding characteristic dimensions of the respective analytes, the present invention enables to dispose the adsorbent materials between the electrodes for detection and identification of the analytes in fluids even the analyte concentrations are sufficient.

It will be appreciated that adsorption process can associate with absorption process, or the adsorption and absorption processes can be happened simultaneously to thereby be the sorption process. However, the exact situation regarding a specific process will be dependent upon facts including types of the materials, sizes including thickness of the materials added between electrodes, allowed times for the adsorption process, and amount of the analyte in analysis. Therefore, the adsorption disclosed herein may include absorption or sorption.

The present invention sensor is electrically connected to the AC device for providing a detectable information of the analyte residing or passing the sensor, wherein the device can be assembled according to various electronic configurations.

The present invention sensor and method has many novel and unique features and advantages for detecting and identifying analytes in fluids. In summary, the core technology utilizes a sensor having first and second groups of the respective integrated electrodes, which are connected by the respective first and second electrically conducting means serving as the respective first and second electrical poles. The present invention sensor possesses properties of high output, reduces physical size and improved electrical characteristics.

The sensor configuration also provides a reference sensor for compensating background influence and selectively detecting known analytes serving as the respective biochemical markers. In addition, the present invention applies a temperature programming including the gradient and constant temperature programming to the sensor for better controlling the adsorption and desorption processes of the analyte residing or passing between the sensor electrodes, which improves the analyte detection and identification.

The sensor configuration also provides a reference sensor for compensating background influence and selectively detecting known analytes serving as the respective biochemical markers. In addition, the sensor applies a temperature programming including the gradient and constant temperature programming to the sensor for better controlling the adsorption and desorption processes of the analyte residing or passing between the sensor electrodes, which improves the analyte detection and identification.

In addition, the present invention has a low cost to manufacture the sensor having a small size, which results in a sensor instrument that is compact in size to make it portable and convenient to use.

These advantages particularly benefit a handheld sensor instrument powered by DC batteries, due to a small size of the sensor that is low power consumption to control the sensor temperature.

It will be appreciated that one of the main advantages of the present invention is to use the invented sensor in the single sensor configuration for simultaneously generating two spectra of the respective patterned AC electrical properties of an analyte from a single measurement. The reproducibility of manufacturing sensors can be easily achieved with the present single sensor configuration when a few pairs of identical sensors are needed for constructing a sensor instrument. The small size of the sensor which results in low power consumption for controlling sensor temperature and small volume requirement also allows the practical implementation of a dual sensor detection which, in addition to an analytical sensor, incorporates a reference sensor having the identical configuration as the analytical sensor.

With the dual sensor detection, samples of analytes in fluids with background subjects such as humidity levels are tested by the analytical sensor while only the background subjects including the fluids are tested by the reference sensor. By comparing the output from the respective analytical and reference sensors, the background effect can be removed from the test results of the respective analytes. Similarly, additional background subjects can also be removed or eliminated, which include the aging effect of the polymer films dispensed into sensors, and changes in the testing responses induced by the temperature variations. Furthermore, application of the dual sensor detection brings an additional advantage of increasing the testing speed since testing of the analytical and reference sensors is completed simultaneously.

These and further novel features and objects of the present invention will become more apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated:

FIG. 4 illustrates a schematic diagram of a sensor 1 in a single sensor configuration containing a pair of metal wires or plates acting as electrodes or a capacitor;

FIG. 4A shows a dual sensor which utilizes two identical sensors 1, one as an analytical sensor 2 (AS in abbreviation), and the other as a reference sensor 3 (RS). FIG. 4A shows the dual sensor 12 without an integrated form of two sensors;

FIG. 4B shows a dual sensor which utilizes two identical sensors, one as an analytical sensor 2, and the other as a reference sensor 3. FIG. 4B shows an integrated form 13;

FIG. 5 shows a diagram for electrically connecting a sensor 1 to an alternating current analyzing device 14;

FIG. 6 shows a schematic of any type of adsorbent materials 11 placed between electrodes or into capacitor for adsorbing analytes in fluids;

FIG. 7A shows a schematic diagram to illustrate a different configuration 4 to form a sensor in the single sensor configuration, where an electrode acting as a first electrode and electrically conductive structure member such as a sidewall acting as a second electrode;

FIG. 8 illustrates a schematic diagram of a sensor 1' having integrated electrodes in a single sensor configuration containing three identical metal conductors serving as the respective electrodes, wherein two outer electrodes are connected in parallel by a first electrically conducting means serving as a first electrical pole, and the middle electrode is connected by a second electrically conducting means serving as a second electrical pole;

FIG. 8A shows a dual sensor which utilizes two identical sensors 1', one as an analytical sensor 2' (AS in abbreviation), and the other as a reference sensor 3' (RS). FIG. 8A shows the dual sensor 12' without an integrated form of two sensors;

FIG. 8B shows a dual sensor which utilizes two identical sensors, one as an analytical sensor 2', and the other as a reference sensor 3'. FIG. 8B shows an integrated form 13';

FIG. 9 shows a diagram for electrically connecting a sensor 1' to the alternating current analyzing device 14;

FIG. 10 shows a schematic of any type of adsorbent materials 11 placed into a gap between two adjacent electrodes of the sensor 1' for adsorbing analytes in fluids;

DETAILED DESCRIPTION OF THE PREFERRED EMBODIMENTS

Figure 1:
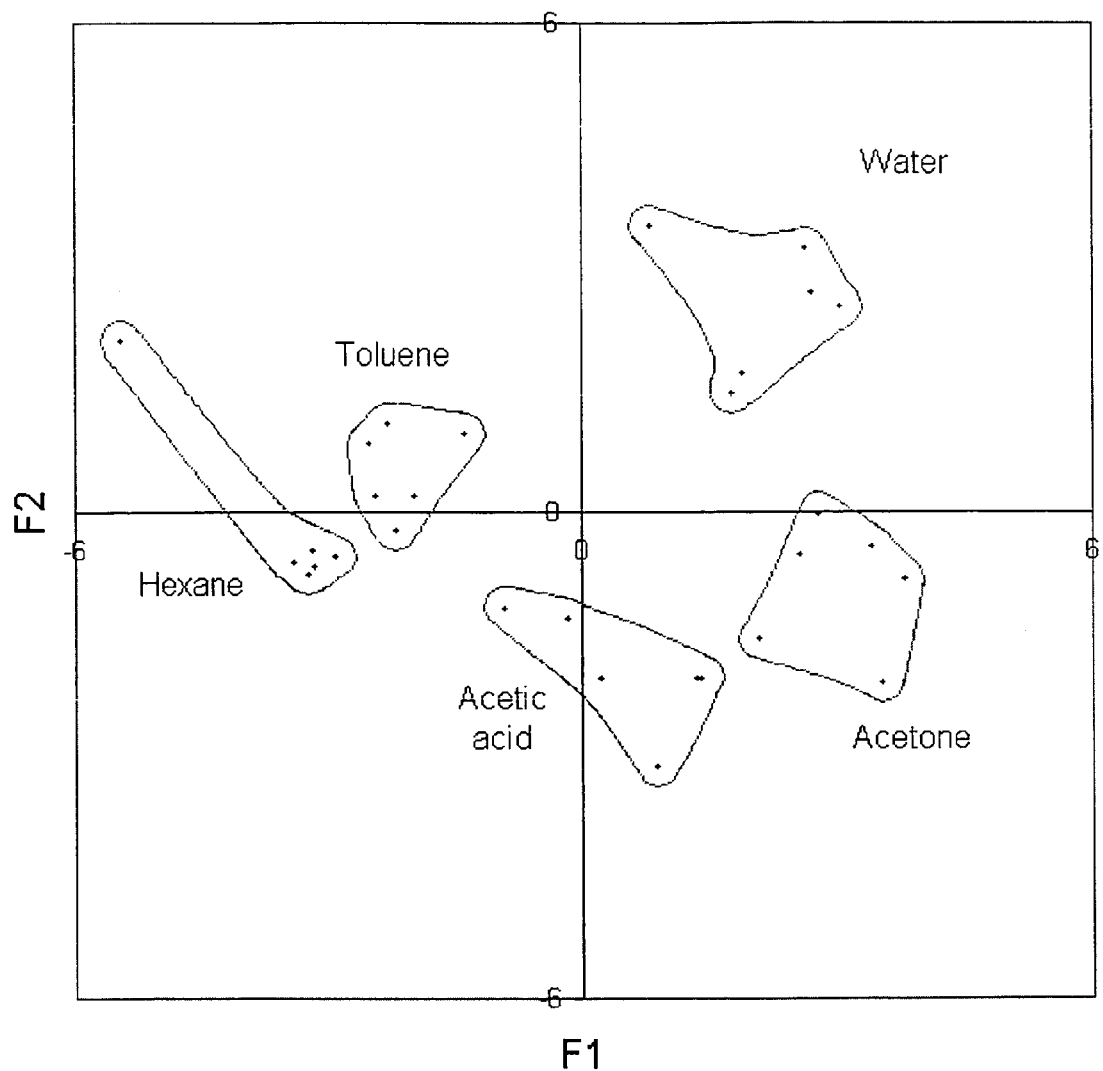
FIG. 1 is an illustrative plot diagram showing the result of classification for five (5) chemicals from a principal component analysis, where resistance and reactance at each of seven (7) frequencies are used in the analysis, wherein the frequencies are randomly selected from the swept 201 frequencies ranging from 10 KHz to 500 KHz.

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Disclosure of the present invention includes two sections. The first section is consistent with the preferred embodiment of the sensor in the single sensor configuration that was initially disclosed by the '425 Sun patent. The second section discloses an improved sensor, which is developed according to the initial embodiment of the sensor.

The present invention sensor and method for detecting and identifying analytes in fluids has two main objectives. Referring to FIGS. 4 and 5, the first major objective is to design a sensor 1 in a single sensor configuration, which has two electrodes operated by an AC excitation of voltage or current at an amplitude having varied including swept frequencies for effective identification of an analyte in a fluid by detecting certain electrical properties which are associated with the distinguished physical and chemical characteristics of the analyte, such as dielectric constant, and polarity or dipole moment that is based on the respective element electronegativities.

This first main objective of the present invention is achieved by applying an electrical frequency sweeping, which is acquired from an alternating current (AC) analyzing device 14 connected to the sensor 1 containing the analyte. Therefore, it obtains two sets of the patterned analyte AC electrical properties according to various swept frequencies from a single measurement, wherein the electrical properties are obtained at each frequency. In this setting, various analytes can be detected. By analyzing the obtained electrical properties of the respective analytes with a pattern recognition process, patterns of the respective analyte electrical properties can be recognized, which are correlated to the respective analytes. Therefore, each of the analytes can be identified by comparing the recognized pattern of the analyte with patterns of known substances. It will be appreciated that the first object reflects a core technology of the present invention.

The second main objective of the present invention is to provide a sensor configuration including a method that can eliminate background influence including effects of the respective humidity levels, polymer aging phenomena and variations of the analyte electrical properties caused by the temperature variations. Referring to FIGS. 4A and 4B, the second main objective is achieved by applying a dual sensor which utilizes two identical sensors 1, one serving as an analytical sensor 2 and the other as a reference sensor 3. The dual sensor has two embodiments, an integrated one 13 and another separated one 12. Alternatively, the present invention dual sensor can be used to identify a chemical or chemicals of an analyte that is a chemical mixture. The application of the dual sensor is particularly useful to selectively test known chemical or chemicals serving as the respective biochemical marker or markers from a biological sample for medical diagnoses.

It will be appreciated that implementation of the dual sensor is practically applicable in the present invention due to the advantage of the small volume of the single analytical sensor that can generate a series of the patterned information for an analyte in fluid in a single measurement.

In the present invention sensor and method, an analyte of interest refers to a chemical having a plurality of molecules with the same molecular formula. The analyte also refers to a specific mixture of different chemicals that are grouped together, wherein each chemical has a plurality of molecules with the same molecular formula, for example, the chemical mixture of a coffee smell. The analyte may not have an odor, such as a chemical of hydrogen, or a mixture of the industrially produced combustible gases without addition of the smell substance. The analyte also may have an odor, for example, as a chemical of acetic acid, or mixed chemicals in perfume, a smell of a bad breath from a living object, or a smell of sewerage. Analytes refer to a plurality of the respective different chemicals or chemical mixtures. The analyte or analytes are in gaseous or liquid phases.

In general, the chemical analytes as the interest of this study can be from materials containing illegal substances (comprising marijuana), environment concerns (comprising air, water and soil pollutant monitoring such as ground level ozones in the air), medical interests including hospital concerns (comprising biological sample including those for medical diagnoses based on finding known biochemical markers or markers such as breath analysis), scientific and research interests including space research interests (comprising study of air quality in space vehicles), interests of industrial sectors including food (comprising freshness testing of meat and fish), beverages (comprising order testing of lemonade), agricultural (comprising testing of fruit ripeness), chemical (comprising monitoring of hydrogen chloride production), petroleum (comprising flammable gas leakage detection), plastic (comprising process and quality control), construction (comprising indoor air monitoring for newly built buildings), pharmaceutical (comprising new drug discovery), automobile (comprising lubricating oil and fluid monitoring), biochemical (comprising biochemical syntheses including from enzyme-catalyzed reactions), and transportation (comprising emission control), consumer interests including perfume, cosmetic, wine and flavor, safety interests (comprising explosive, arson, and road spill investigation) and military interests (chemicals used as weapons).

The fluid in this disclosure refers to a chemical background in either gaseous or liquid phases, which is not of interest in the study. The fluid serves to "host" the analyte or analytes. In a pure condition of the analyte in the fluid, the analyte itself can serve as the fluid. In a situation when the analyte and fluid are mixed together, a fluid can either be a chemical or a chemical mixture. For example, in the case of studying air pollutants, the air that is a mixture of various gases is the fluid to host the gaseous pollutants. In the case of a GC, the hydrogen or nitrogen or helium as a carrier gas is served as the fluid to carry out various separated chemicals that is originally of a chemical mixture.

Fluids refer to a plurality of the respective different chemicals or chemical mixtures. For example, in a study of bad breath caused by dental diseases for a plurality of patients, a biochemical marker gas of hydrogen sulfide is the analyte of interest, which is common to all the patients' breath samples. Obviously besides the marker gas, a breath sample from a patient is comprised of additional chemical gases that are not the interest of study, which are referred to a fluid. However, compositions of additional chemical gases are different for different patients. Such as, percentages of the respective produced carbon dioxide and unconsumed oxygen, which are part of the additional chemical gases of the breath, are dependent upon each patient's health conditions including the lung function and blood system function. Therefore, the breath samples of all patients, which are tested, have the same marker gas but different fluids. In this situation, it refers to a sample group as "an analyte in fluids" of this disclosure.

Following the above analogy, in study of patients' breath samples for medical diagnoses of different organ diseases such as lung, kidney and intestine diseases, the breath samples are comprised of the respective different marker gases as the study interests in the respective different fluids. They are referred to "analytes in fluids" of disclosure.

Opposite to the above defined sample group "analyte in fluids", there is a sample group "analytes in a fluid". For example, a same carrier gas (or solvent) is served as a continuous fluid to host different chemicals separated in the gas (or liquid) chromatographic process, wherein the chemicals are from an initial analyte that is a chemical mixture. Another example is from a regional air pollution case, where the same air hosts various different pollutants according to different areas of the region. It will be appreciated that, the case of "analytes in fluid" in the chromatographic process is a special one, wherein it is the process that separates the initial analyte of the chemical mixture into various analytes of the respective chemicals in series, which are separately positioned in the same fluid to thereby are individually detected.

However, it will be appreciated that, no matter of what kinds of sample groups in studies of the analyte detection and identification, each sample must be sequentially tested by the sensor instrument. Therefore, for a general disclosure of testing the above defined sample groups: "analytes in fluid", "analyte in fluids" and "analytes in fluids", it comprises the sequential steps of testing, where each individual sample is sequentially tested. Regarding each tested individual sample at a testing moment, it only contains an analyte in a fluid for the above defined analytes and fluids.

Chemicals are well known to have the respective distinguished dielectric constants. They also contain various chemical elements that have the respective distinguished electronegativities. In addition, at a molecular level, chemicals have the respective unique molecular structural configurations, sizes, weights, shapes including symmetries, and dipole moments. These factors determine physical and chemical characteristics of the respective chemical analytes, and affect the adsorption and desorption processes of the respective chemical analytes interacting with sensor electrodes.

These physical and chemical characteristics can be described with certain AC electrical properties of the respective analytes, such as, current, voltage and impedance Z including the phase sensitive components: reactance X, resistance R, and phase angle $\theta$, as the respective analytes are excited by an AC signal at a frequency. The AC excitation signal herein refers to an alternating current or voltage in the form of sinusoidal waves.

Referring to FIG. 5, the AC electrical properties can be obtained by using an instrument impedance analyzer or any other known alternating current analyzing device 14 connected to the sensor 1 with a substrate 10 wherein the sensor is positioned thereonto. In its simplest form, the sensor 1 with the air substrate serving as the test device can be a pair of metal wires or plates acting as spatial electrodes or a capacitor. The paired electrodes of the sensor can also be positioned onto the respective ceramic or silicon substrates to be the respective thick or thin film electrodes. The AC electrical properties of the sensor, as the detectable information of a sample of an analyte present in a fluid, are obtained as the sample resides or passes between the electrodes or capacitor.

Impedance is described as $$Z=R+X \quad [2]$$

in complex (with the bold letters indicating vectors). The phase angle $\theta$ can be calculated from the R and X values.

Reactance X of the sensor from the present invention is combined with a reactive capacitance $X_C$, and reactive inductance $X_L$, which can be described as follows:

$$X_C=j(-1/2\pi fC) \quad [3]$$

$$X_L=j(2\pi fL) \quad [4]$$

where C is a capacitance that is proportional to a dielectric constant of a medium residing between two electrodes, and L is the inductance of the electrode. For a short electrode of the present invention, the value of inductance L is small and the reactance X is predominantly capacitive. Thus the reactive capacitance $X_C$ is a good approximation of the reactance X.

Therefore, if in the presence of an analyte in a fluid between the electrodes, the reactance is X(2). If in the absence of the analyte the reactance is X(1), which is the contribution of the fluid, then their difference $\Delta X$:

$$\Delta X=X(2)-X(1) \quad [5]$$

can be obtained, which is change of the reactance as the electrical contribution of the presented analyte.

Since the capacitance of the analyte is governed by the dielectric constant and reactive capacitance is predominant of the reactance, the reactance can be used to detect and identify the analyte. This means reactance provides a signature information of each chemical or chemical mixture. By varying including sweeping the frequencies in a single measurement, the present invention is able to construct a reactance spectrum to record chemical characteristics of the analyte at each of the varied including swept frequencies. Therefore, the spectrum contains a series of the patterned AC related electrical properties of the analyte.

Analytes will be adsorbed by surface of the test device through the chemisorption and physisorption processes. This capability creates a complicated diffusive process, and surface interfacial kinetics or surface resistance for the analytes, which are associated with their distinguished molecular characteristics. For example, exposure to volatile organic compounds including those rich in hydrogen or oxygen noticeably changes the electrical conductivity of metal oxide sensors (see the Nagle and Blaster Publications).

Since each chemical element of analytes such as oxygen or hydrogen or nitrogen or carbon has its defined electronegativity, which contributes to the polarities or dipole moments of the respective analytes, the change of conductivity (resistivity) indicates that resistance can be used to record chemical characteristics of the respective analytes.

In the present invention, a series of resistance information is also simultaneously generated with varying frequencies and applying a vector analysis in the same single measurement, where the reactance information is obtained. The change of resistance at each frequency is defined as:

$$\Delta R = R(2) - R(1) \quad [6]$$

where $R(1)$ is the resistance of a fluid in the absence of any analyte and $R(2)$ is the resistance of the electrodes exposed to an analyte in the fluid. The change of resistance is the contribution of the analyte.

Comparing magnitude of resistance and reactance of an analyte, it will be appreciated that reactance is predominant over the resistance, which governs values of impedance since the analyte in the fluid is not conducting in the dry condition. It will be also appreciated that phase angles $\theta$ can be calculated from R and X. Therefore, the change of phase angle $\theta$ is also readily available. Combining the information of change of reactance and resistance and/or change of phase angle at each frequency, a plot of containing curves of the respective reactance, resistance and phase angle is constructed over the varied including swept frequencies, which shows a patterned electrical information of the analyte. Therefore, in a general practice, the plotted curves of the analyte can be first studied for their characteristics including through comparison with curves of known analytes that have been already established in a database, so that the characteristics including similarity, or dissimilarity, or a pattern of the electrical information of the analyte may be recognized through directly analyzing the plotted curves.

Following the above disclosed processes, a plurality of different analytes can be tested, which results in obtaining a plurality of the respective patterned analyte AC electrical properties.

Besides the plotted curves which are in a continuous data form of the patterned analyte electrical properties, a discrete data form of the properties can also be established by constructing a matrix of the analyte characteristic electrical properties. The matrix comprises an even number of columns, wherein each two adjacent columns are for inputting the respective analyte electrical properties at one frequency, for example reactance and resistance data. Therefore, the matrix has a maximum number of the column that is twice of the number of the varied including swept frequencies (see specification of the manufactured analyzing device on the number of collected frequencies), or, the column number can be dependent upon a number of frequencies that are randomly or specifically selected within the varied frequencies. A row represents obtained electrical properties of one measured analyte according to the listed frequencies in the matrix. Obviously, the same analyte can be measured multiple times in the experiment.

Following the above disclosed procedure, a matrix can be established for a plurality of analytes, wherein one row represents obtained electrical properties of one of the analytes according to the selected frequencies if each of the analytes is measured one time.

As the change of the AC electrical properties, which varies nonlinearly with varying frequencies, variations in the changes of the respective characteristic electrical properties, which are presented in the matrix for the tested analytes, can be analyzed through application of various known analysis algorithms, which comprise multivariate analysis method that includes various pattern recognition algorithms. Applying such analysis including pattern recognition analysis on the matrix of the analyte electrical properties, characteristics including patterns of the respective analytes can be easily recognized, as compared with the difficulty in finding patterns through directly analyzing the plotted curves of the respective analytes.

As a result, an analyte can be identified by comparing the recognized pattern of the characteristic electrical properties of the analyte with patterns of known substance from a database that has been already established.

It will be appreciated that, although the preferred frequencies of the present invention are varying including sweeping from 10 KHz to 1 MHz, other frequencies, which are different from the preferred frequencies, can also be applied according to the principle and scope of the present invention. However, applying the preferred frequencies can not only identify the analytes but also increase the options of instrument design and practical application.

The present invention sensor design does not require the use of any conductive polymer film for detecting or identifying analytes at sufficient concentrations. This is because the AC excitation signals can be applied across the vacuum, they can be across the gap of the two electrodes without conductive materials placed in between. This is particularly suitable to be used as a detection of chromatographic methods including GC and LC (a liquid chromatography), where each chemical of the chemical mixture is separated and concentrated in the chromatographic process. This new detection method will provide information on not only the quantities but also the identities of the respective analytes. Besides, this new detection is non-destructive and universal, which are additional key advantages.

The present invention sensor design does not require the use of any conductive polymer film for detecting or identifying analytes at sufficient concentrations. This is because the AC excitation signals can be applied across the vacuum, thus they can be across the gap of the two electrodes without conductive materials placed in between. This is particularly suitable to be used as a detection of chromatographic methods including GC and LC (a liquid chromatography), where each chemical of the chemical mixture is separated and concentrated in the chromatographic process. This new detection method will provide information on not only the quantities but also the identities of the respective analytes. Besides, this new detection is non-destructive and universal, which are additional key advantages.

In addition, referring to FIG. 6, since AC signals can travel through vacuum, the present invention can use any type of adsorbent or absorbent or sorbent materials 11, whether or not they are electrically conductive, for detecting analytes in fluids from concentrating or selectively concentrating dilute analytes. Thus the present invention can utilize a variety of developed and known techniques on concentrating analytes or selectively concentrating chemical marker or markers of the respective analytes in fluids to improve sensitivities and selectivities of the sensors. Such techniques typically involve application of polymer films, polymer inorganic materials composites, composites containing particles of the platinum group metals, solid inorganic materials used as stationary phase in the gas adsorption chromatography, and polymeric materials used as stationary phase in preparation of packed and open tubular columns in the gas partition chromatography.

For example, hydrogen is an important industrial gas for many applications. It is also critical to detect and identify the hydrogen gas for safety concerns. In the present invention, the hydrogen gas can be selectively concentrated by applying composites containing palladium particles, composited by organic or inorganic fillers. This is because the hydrogen gas has a large solubility in the palladium metal that can absorb up to 900 times its own volume of hydrogen (Hand Book Of Chemistry And Physics, CRC Press, 24th Edition, 4-21, 1993-1994). For this reason, palladium is often referred to as a "hydrogen sinker". Since the analyte detection of the present invention is not limited to the adsorbent materials that are electrically conductive, it has a great flexibility to choose any percentage of palladium metal including its particle form in the composite, according to concentration of the hydrogen gas in fluid, to concentrate and then detect the hydrogen gas in the application of the present invention.

In addition, palladium is one of the platinum group metals, consisting of ruthenium, rhodium, palladium, osmium, iridium and platinum. They have similar physical and chemical properties including the hydrogen solubility (Hand Book Of Chemistry And Physics, CRC Press, 24th Edition, 4-15 to 4-25, 1993-1994). Therefore, each metal of the platinum metal group is appropriate in the application of the present invention.

Furthermore, the gas adsorption chromatography uses solid particles as stationary phase to selectively adsorb molecules. Various solid inorganic materials can be used for this purpose. Among them, molecular sieves, silica gel, alumina, glass, porous carbon particles, and calcium carbonate are the most popular choices. In addition, fluorocarbon powders are also appropriate, such as tetrafluoroethylene polymer particles. Illustration of these basic materials can be found elsewhere (Poole, C. F.; Poole, S. K.; Chromatography Today, 199-209, Elsevier Science Publishers. B. V., 1991, and references cited therein).

For example, molecular sieves are materials containing fine pores of precise and uniform sizes, which can be controlled in manufacturing. The molecular sieves have been known and used as the adsorbent materials for gases and liquids. They retain adsorbates by strong physical forces, and separate molecules based on their sizes, configurations, polarities, and degrees of unsaturation. Molecular sieves will adsorb carbon monoxide in preference to argon. They preferentially adsorb polar molecules containing oxygen, sulfur, chlorine, or nitrogen atoms, and asymmetrical molecules containing oxygen, sulfur, chlorine, or nitrogen atoms, and other asymmetrical molecules. Molecular sieves also effectively retain water and carbon dioxide and trap ethylene or propylene from saturated hydrocarbons.

In gas partition chromatography (GC), separation of chemicals in a mixture is based on vapor pressure of chemicals and selective interactions between chemicals and polymeric materials used as the stationary phase of the GC columns. The stationary phase materials are coated onto the solid supports for the packed columns or interior surfaces of the open tubular silica capillary columns. At the molecular level, the interaction is based on intermolecular forces between each chemical and materials of the stationary phase such as dispersion, induction, orientation, and donor-acceptor interaction. To help the understanding of the processes described above, a term "like dissolves like" may be useful to explain results of such intermolecular interactions. Selectivity is one of results of the interactions due to a similarity between "likeness" of a kind of chemicals and materials of the stationary phase of the column. For example, polarities are characteristic parameters for the respective chemicals and thus can be used to describe such likeness. Polar chemicals like polar materials of the stationary phase, and non polar chemicals go to non polar stationary phase.

Based on this principle, objective of selective partition of a series of chemicals can be achieved by using a kind of stationary phase materials whose polarities are close or match the polarities of the respective chemicals. For example, polysiloxane is well known as a nonpolar material. It is most popularly used as the base materials of the GC stationary phase since its basic chemical structure can be readily derived by methyl, vinyl, phenyl, diphenyl, 3,3,3-trifluoropropyl, 2-cyanoethyl, or 3-cyanopropyl constituents to change its polarity from non polar to polar, which is known elsewhere (Poole, C. F.; Poole, S. K.; Chromatography Today, Chapter 2, 105-229, Elsevier Science Publishers. B. V., 1991, and references cited therein; Hyver, K. J., Editor; Sandra, P., Guest Author; High Resolution Gas Chromatography, 2-1 to 2-16, $3^{rd}$ Edition, Hewlett-Packard Co., 1989, and references cited therein). Therefore, specifically derived polysiloxane polymers are appropriate to many types of chemicals in terms of closeness of their polarities.

The following are examples of the well known derived polysiloxane polymers that are often involved in applications of selectively partitioning various chemicals in fluid:

1. Poly(100% dimethylsiloxane) for analytes of solvents, petroleum products, fuel, oil, hydrocarbons, pharmaceuticals, flavors, fragrances, sulfide compounds, and PCBs.
2. Polymers containing (5% diphenyl/95% dimethyl), or (35% diphenyl/65% dimentyl), or (14% cyanopropyl/86% dimethyl) for analytes of pesticides, aromatic hydrocarbons, polychlorinated biphenyl, oxygenates, amines, essential oil, pharmaceuticals, environmental samples, and nitrogen containing chemicals including herbicides.
3. Poly(20% diphenyl/80% dimethylsiloxane) for analytes of flavor aromatics and alcoholic beverage.
4. Polymers containing (50% phenyl/50% methyl) or (trifluoropropylmethyl) for analytes of environmental chemicals, solvents, ketones, drugs, steroids, glycols and halogenated compounds.
5. Poly(65% diphenyl/35% dimethylsiloxane) for analytes of phenols and fatty acids.
6. Poly(50% cyanopropylmethyl/50% phenylmethylsiloxane) for analytes of carbohydrates and neutral sterols.

It will be appreciated that, as above illustrated, the derived polysiloxane can selectively interact various chemicals of interest including the amines. The amines including the respective derivatives have been reported by many researchers as the targeted biochemical markers of patients' specimens including the breath samples from the medical diagnoses of many diseases. Some of the research results are listed in the '333 Lewis patent, which are incorporated herein by references in the entirety for simplifying disclosure of the present invention.

Besides the derived polysiloxane, the meta-linked poly (phenyl ethers), phthalate ester, polyester, polyethers such as poly(ethylene glycols) and liquid organic salts are also popularly used in GC for interacting chemicals having the respective polarities. For example, poly(ethylene glycols) is a polar phase, which is particularly for analysis of acids, alcohols, aldehydes, acrylates, nitriles, ketones, essential oils, glycols and solvents. The liquid organic salts are polar, comprising organoammonium or organophosphonium cations coupled with nucleophilic anions such as sulfonates or inorganic anions such as chlorides, bromides and nitrates. Examples are tetrabutylammonium sulfonate and tetrabutylphosphonium nitrate (Poole, C. F.; Poole, S. K.; Chromatography Today, 114-118, and references cited therein; Hyver, K. J.; Sandra, P.; High Resolution Gas Chromatography, 2-9).

Polymers including the above disclosed derived polymers can be coated onto solid support particles for preparation of the packed columns or onto the interior surfaces of the respective silica capillary columns with the existing procedures that are known elsewhere. Before coating the polymers, deactivation is a common preparation procedure for treating surface of the packing particles or interior surface of the capillary column, wherein the deactivation is performed to maintain or enhance the wettability of the surface for achieving a uniform polymer firm coated on the surface, which is also known elsewhere.

In general deactivation is conducted by converting surface silanol groups of the solid support or silica column to silyl ethers by reaction with dimethyldichlorosilane (DMCS), hexamethyldisilazane (HMDS), trimethylchlorosilane (TMCS), or a combination of these reagents, and octadecyldimethylchlorosilane (Poole, C. F.; Poole, S. K.; Chromatography Today, 122-123, 137-148, and references cited therein).

Additionally, it is also popular for chemical modification of solid support particles or fused silica capillary columns to form bonded phases in GC column manufacturing. One approach involves reaction of monofunctional or multifunctional alkylsilane or cyclosiloxane reagent with silica or diatomaceous support particles or fused silica columns. In the reaction, chemical attachment via formation of siloxane bonds and polymerization are probably both involved in bonding the stationary phase to the support particles or columns. The other approach includes application of peroxide-induced or ozone-induced free radical crosslinking reaction of coated packings to form immobilized polysiloxane phases. For example, moderately polar polysiloxane phases are prepared with various amounts of vinyl, tolyl or octyl groups, which increase formation of the crosslinking polymer (Poole, C. F.; Poole, S. K.; Chromatography Today, 122-127, 132-152 and references cited therein).

Therefore, it will be appreciated that the present invention can apply the above disclosed successful known techniques to treat the surface of the ceramic or silicon substrate of the respective thick film or thin film electrodes of the single sensor 1, or the solid supports for use in the spatial electrodes, so that uniform polymer films can be achieved in the present invention.

Applying a sensor with AC electrical frequency varying including sweeping technique, the present invention can not only obtain a patterned information of each analyte but also gain a distinct advantage of having small sizes of the respective sensor and sensor compartment in sensor design. The small sizes of the respective sensor and its compartment make the present invention practical to be utilized as a dual sensing detection device in sensor manufacturing, particularly for manufacturing handheld and battery powered electronic nose instruments.

In the dual sensor detection, the present invention applies two identical sensors, one serving as an analytical sensor and other one as a reference sensor. When background subjects, such as humidity, are critical factors that affect sensor performance, an analyte in a fluid with background subjects are tested with the analytical sensor, but only the fluid and background subjects are tested with the reference sensor. By subtracting electrical properties of the analytical sensor from those of the reference sensor, the influence of background subjects, including humidity, can be eliminated. Therefore, the information of the analyte can be obtained without the error introduced by the background subjects.

One application of the this dual sensor arrangement is for in situ medical diagnoses of patients, for example detecting patient ear and mouth diseases. In such diagnoses, analytes of the chemical vapors generated by bacteria caused by diseases are overlapped by the humidity in breath samples, where the water concentration in humidity is significantly higher than concentrations of the analytes. Therefore, the present invention can remove humidity influence during testing the breath samples.

Applying the dual sensor detection to eliminate background subjects including humidity for testing breath samples, the present invention can effectively detect and identify analytes by selectively detecting the respective volatile chemicals that are served as the respective biochemical markers of various diseases for medical diagnoses. This detection for the medical diagnoses is based on established correlation of biochemical markers and the respective organ diseases. In this study, an analyte is generally a chemical mixture, comprising one or several biochemical markers among various chemicals in the analyte.

Applying this detection, a sample having an analyte in fluid with background subjects are tested with the analytical sensor. But only the background subjects and analyte without the marker(s) in the fluid are tested with the reference sensor, which is after removing the marker(s) of the analyte from application of appropriate adsorbent materials to selectively trap the marker(s) prior to measure the reference sensor (see FIG. 12). By subtracting electrical properties of the analytical sensor from those of the reference sensor, only the biomarker electrical information can be obtained.

The following sets forth some published bio-markers of diseases for medical diagnoses:

(1) Methylamine for the kidney and liver diseases, a news report of Feb. 25, 2008, Bio-Medicine, an online of organization to report results of researchers at a joint institute of National Institute of Standard and Technology and University of Colorado at Boulder USA (hereafter "BioMed);

(2) Ammonia and trimethylamine for the renal failure, reported by the respective BioMed and Jacoby, M, Chemical & Engineering News (C&EN), Chicago 2004 for 2004 Pittcon.

(3) Acetone for diabetes, reported by the BioMed, and Chakrabory, S., et al., Current Science, Vol. 94, No. 2, January 2008;

(4) Nitric oxide for respiratory diseases including asthma and lung diseases, reported by the BioMed; Choi, J., et al., Biological Research For Nursing, Vol. 7, No. 4, 241-255 (2006) and Formanek, W., et al., Respiratory Journal, 2002, 19, 487-491;

(5) Ammonia for blood urea nitrogen, reported by Narasimhan, L. R., et al., PNAS, Apr. 10, 2001, Vol. 98, No. 8, 4617-4621;

(6) Pentane for the intestinal inflammation, reported by Kohoszka, J, et al., Diseases of the Colon & Rectum, Vol. 36, No. 6, 597-602, June 1993;

(7) Carbonyl sulfides for cystic fibrosis of lung diseases, reported by Vasich, T, UC Newsroom, UC, Oct. 17, 2005 for UC Irvine research results, and also published in the October 2005 online version of Proceedings of the National Academy of Sciences;

(8) Isoprene for cholesterol, reported by Jacoby, M, C&EN, Chicago 2004 for 2004 Pittcon; and (9) Hexane, methylpentane, o-toluidine and aniline for lung cancer, reported by O'Neil, H. J., et al., Clinical Chemistry, 1988, 34, 1613.

Certain biochemical markers have been studied for their physiological basis. For example, acetaldehyde is for the ethanol metabolism, acetone for decarboxylation of acetoacetate, ammonia for protein metabolism, carbon monoxide for production catalyzed by heme oxygenase, carbonyl sulfide, carbon disulfide, ethanol, hydrogen and methane for gut bacteria, ethane for lipid peroxidation, hydrocarbons for lipid peroxidation/metabolism, isoprene for cholesterol biosynthesis, methanethiol for methionine metabolism, methanol for methanolism of fruit, methylamine for protein metabolism, nitric oxide for production catalyzed by nitric oxide synthesis, and pentane for lipid peroxidation (Risby, T. H., Solga, S. F., Appl. Phys. B, 85, 421-426, 2006).

In addition, a number of biochemical markers have been used in clinical tests, such as acetate for orocecal transit time, aminopyrene, caffeine, erythromycin, galactose, methacetin for liver function, glucose for insulin resistance, glycosyl ureides for orocecal transit time, ketoisocaproate and methionine for liver mitochondrial function, linoleic acid for fatty acid metabolism, phenylalanine for phenylalanine hydrolase activity, triolein for fat malabsorption, uracil for dihydropyrimidine dehydrogenase activity, and urea for *H. Pylori* infection (Risby, T. H., Solga, S. F., Appl. Phys. B, 85, 421-426, 2006).

It will be appreciated that the bio-markers also exist in patient urine, stool, serum, blood and saliva samples, so that the present invention including the dual sensing strategy also can be applied to test headspace of these samples for medical diagnoses.

Breath samples have been recently used for diagnoses of the breast cancer (Alvarez, M, Fox News USA, reported on Feb. 28, 2008 for research at University of Michigan, and Dobson, R., Mail Online, at 2 Derry Street, London W85TT UK, reported on Jun. 5, 2008 for research conducted including at Imperial College in London).

Besides using them for medical diagnoses, the breath samples also can be used to monitor anaesthetic (propofol) of patients during surgery, since there have been found the propofol and two metabolites (2,6 di-isopropyl quinone and 2,6 di-isopropyl quinol) presented in the breath samples (Harrison, G. R., et al., British Journal of Anaesthesia, 2003, Vol. 91, No. 6, 797-799).

Human body odor is also of interest to study in the field of the medical diagnoses. For example, a typical skin odour of individuals is observed in the presence of schizophrenia (Smith, K., et al., Science, 1969, 166, 398). Recently, application of electronic nose instrument to study the skin odor includes detection of the schizophrenia (Di Natale, C., et al., Sensors and Actuators B, 2000, 65, 216). In addition, gaseous sample collection is also known long time ago (Gardiner, A. J., et al., Archives of Disease in Childhood, 1981, 56, 125-127). Therefore, the present invention also can study the body odor, through an in situ testing or testing the collected samples of the body odor, including those from foot, armpit and crotch areas, where bacteria are most likely to exist and grow to thereby cause the respective diseases.

In addition to correction of the humidity level as the background influence in application of the dual sensor arrangement, the present invention also can compensate other background influences such as the polymer film aging effect, and variations of the electrical properties caused by temperature variations.

Analytes will be influenced by temperature in the adsorption and desorption processes. In GC, a temperature programming including the gradient temperature programming is often applied for efficient separation of chemical mixture. Because of the small sizes of the respective sensor and sensor compartment which result in low power consumption for temperature regulation on the sensor compartment including the sensor and analytes, the present invention can utilize temperature programming including the gradient and constant temperature programming to control adsorption and desorption processes on the analytes in the interaction with sensor electrodes. This is particularly benefit to the battery-powered and handheld electronic nose instrument of the present invention. Therefore, implementation of the temperature programming makes it possible that chemical characteristics of the analytes can be fully explored by the present invention method.

The present invention facilitates the design and development of the sensor instrument to have a small size, low cost and great portability. As an example, the present invention single sensor is well suitable for a disposable electrode configuration in the design of an electronic nose instrument.

Examples (I)

The following are examples and experimental information of the present invention, regarding the sensor in the single sensor configuration operated by the electrical frequency varying including sweeping technique as the core technique of the present invention, which are offered by way of illustration only and not by way of limitation and restriction.

A pair of electrodes were constructed with gold wires. The electrodes were 12 mm in length and had a gap approximately 1 mm. The electrodes through standard coaxial electrical cables were connected to an AC analyzing device, such as an "Agilent 4294A" impedance analyzer (Agilent, Palo Alto, Calif. USA). Calibration of electrodes was proceeded prior to sample measurement. A frequency sweeping method was used in impedance measurement, where resistance and reactance or impedance and phase angle were simultaneously obtained at each of various swept frequencies. The first experiment was conducted applying frequencies swept from 10 KHz to 500 KHz, and the second experiment used frequencies from 500 KHz to 1 MHz.

Five chemicals as the analytes were used in impedance tests, including acetone, acetic acid, hexane, toluene, and water. In the first experiment, each chemical was alternatively measured six times. In doing so, each chemical was filled a half full into six vials, which were tightly sealed except for sample testing.

Before measuring each chemical sample, room air was first measured and recorded, and its impedance, resistance, and reactance were used as references. To measure a sample, a vial containing such sample was unsealed and placed where the liquid surface was close to the electrodes. A cotton ball was used to block a joint area of the electrode cables and vial opening to prevent variation of chemical vapor concentration inside the vial. Then a waiting period of ten seconds were applied before taking the electrical property data. After the measurement was done, the vial was immediately taken away from the electrodes and resealed. The measured vial was not reused.

The electrodes were then exposed to room air again for about ten minutes before the next measurement. The sequence of measuring chemicals was in the order of toluene, acetone, hexane, water, and acetic acid. The second and subsequent (up to the sixth) measurements were taken with the same sequence. Change of an electrical property is obtained from the following equation, which is the contribution of the respective tested chemicals:

$$\text{Change of electrical property} = \text{Electrical property of sample} - \text{Electrical property of air} \quad [7]$$

Thus a raw data matrix was constructed from collecting electrical properties of the respective chemicals at various frequencies, which were randomly selected from the swept frequencies. Each two adjacent columns of the matrix represented resistance change and reactance change at one frequency, respectively, and each row represented a single measurement of a chemical. Analysis of the data in the matrix was conducted by application of a software having a PCA algorithm, which was installed in a personal computer.

Referring to FIG. 1, there is shown the principal component analysis (PCA) for chemicals of acetic acid, acetone, hexane, toluene, and water with the respective resistance and reactance data obtained at the frequencies as 10, 20, 50, 100, 200, 300 and 500 KHz, which were randomly selected from the various swept frequencies. As illustrated, the electrical information of the chemicals is simplified after applying the principal component analysis and presented in accordance with two principal components F1 and F2. During data analysis applying PCA, the raw data of change of resistance and reactance in the matrix was normalized to the length one before further processing.

It is clear from the graph of FIG. 1 that the test results from the same chemical are grouped in a particular area, as the five chemicals are separated and located in different areas of the F1 and F2 plane. In other words, with the aid of the PCA, a pattern of distributing five chemicals was recognized in the first and second principal component plane. The results of the first and second principal component plotting indicate that chemicals can be distinguished with their respective electrical properties, such as impedance and its phase sensitive components (i.e., resistance and reactance) obtained at each of the swept frequencies ranging from 10 KHz to 500 KHz.

Figure 2:
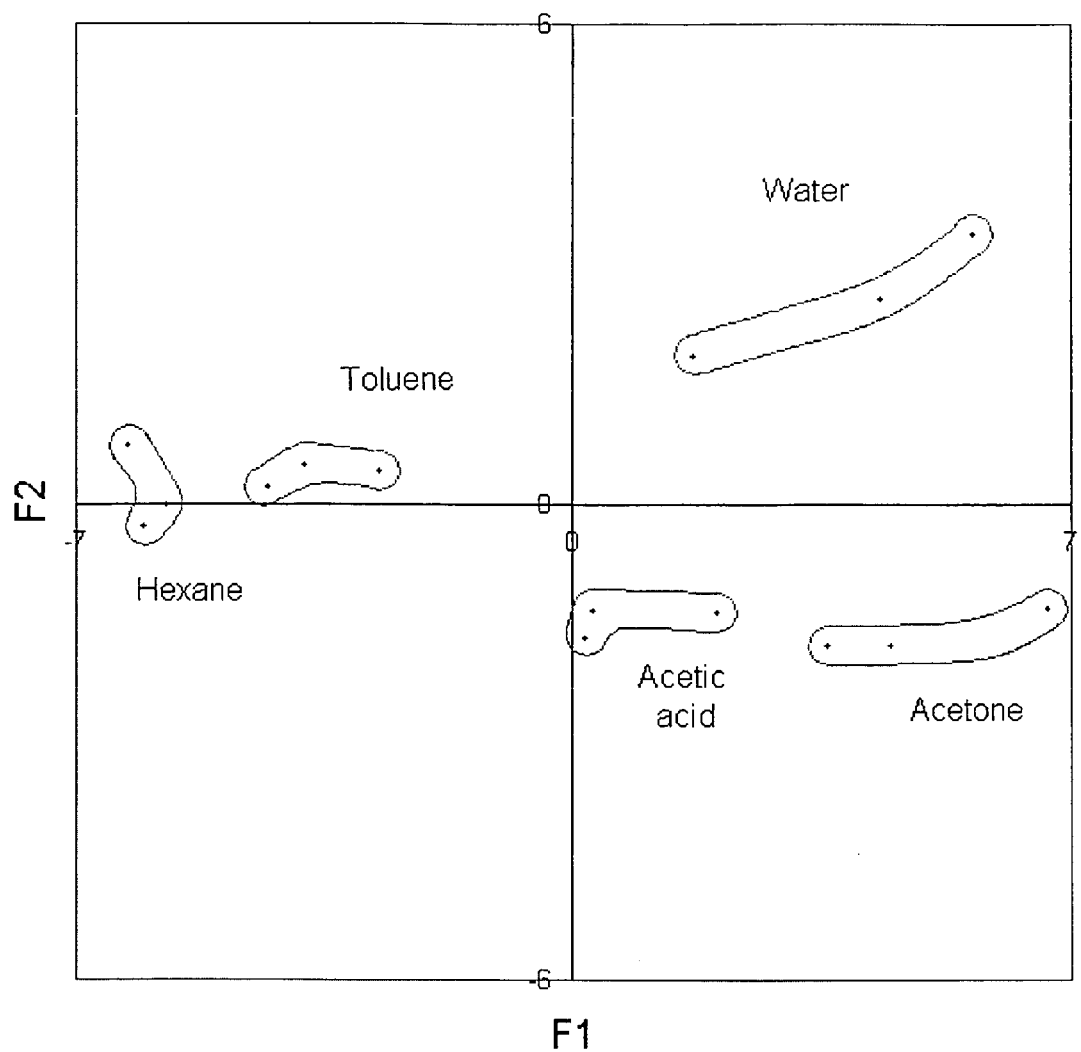
FIG. 2 is an illustrative plot diagram showing the result of classification for five (5) chemicals from the principal component analysis, where resistance and reactance at each of eleven (11) frequencies are used in the analysis, wherein the frequencies are randomly selected from the swept 201 frequencies ranging from 500 KHz to 1000 KHz.

Referring to FIG. 2, there is shown the results of separation from the principal component analysis for the same chemicals of acetic acid, acetone, hexane, toluene, and water, where their resistance and reactance data were obtained at the randomly selected frequencies 502, 550, 600, 651, 700, 750, 801, 850, 901, 949 and 1,000 KHz among the swept frequencies. In the second experiment, each chemical was repeatedly measured three times in accordance with the procedure described above. During data analysis applying the PCA, the raw data matrix of change of resistance and reactance was normalized to the length one before further processing. The results indicate that impedance and its components can be used to identify chemicals, according to a pattern of the respective five chemicals that are distinguishably distributed in the first and second principal component plane.

A third experiment was conducted to test three analytes of acetone, toluene and a liqueur containing approximately 44% alcohol that is belong to a chemical mixture. The experimental conditions were generally the same as those illustrated above, except for: (1) The electrodes were 13 mm in length and had a gap approximately 0.5 mm, which were made of wire leads cut from commercial resistors. The leads were copper wires coated with tin metal film; (2) each analyet was stored in one vial that was reused in the experiment; (3) five measurements were conducted for each analyte, and (4) resistance and reactance at seven frequencies of 10, 20, 50, 100, 200, 300 and 500 KHz were used for data analysis, wherein the frequencies were randomly selected among frequencies swept from 10K to 500 KHz.

Figure 3:
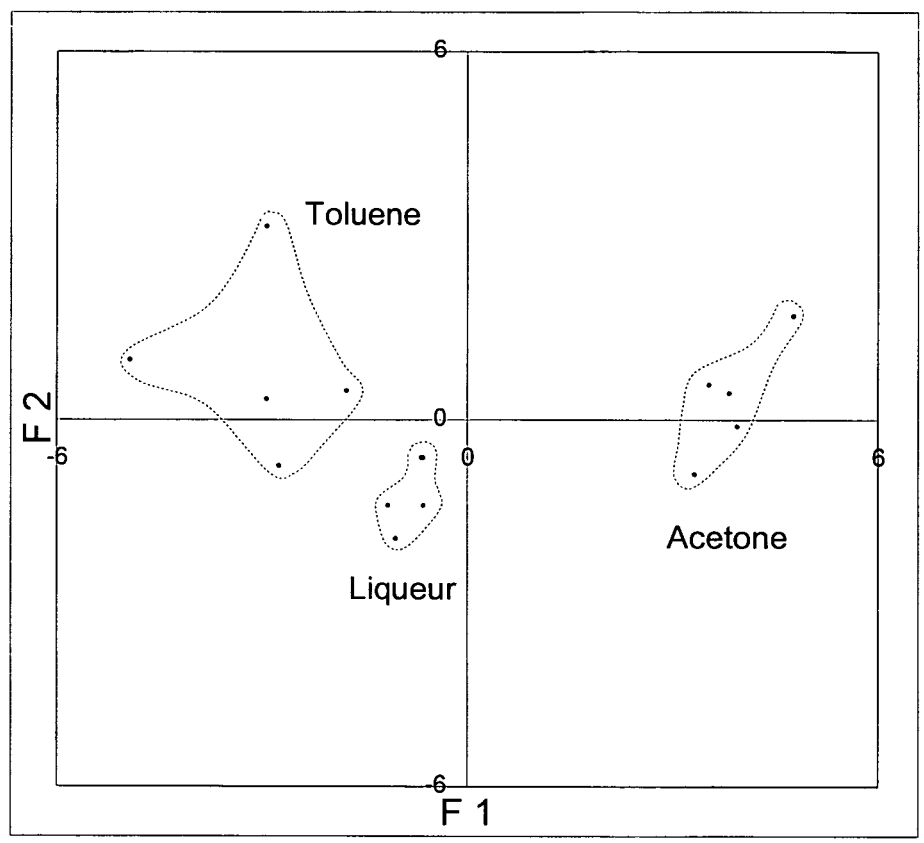
FIG. 3 is an illustrative plot diagram showing the result of classification for three (3) analytes from a principal component analysis, where resistance and reactance at each of seven (7) frequencies are used in the analysis, wherein the frequencies are randomly selected from the swept 201 frequencies ranging from 10 KHz to 500 KHz.

Referring to FIG. 3, results of the third experiment indicate that impedance and its components can be used to identify chemicals, according to a pattern of the respective three analytes that are distinguishably distributed in the first and second principal component plane. It will be appreciated that the liqueur is an analyte being a chemical mixture of water, alcohol having ethanol as the main ingredient, and various other volatile hydrocarbons. Therefor, the headspace of the liqueur also contains those mixed chemicals. This experiment demonstrates that electrical properties can be used to distinguish analyte of the chemical mixture, as compared with other analytes that are the respective different chemicals.

It is will be appreciated that the application of the above specified frequencies is only for illustration of effectiveness according to the principle and scope of the present invention. It is not intended here to restrict other frequencies, which are different from the swept frequencies that have been disclosed above in application of the present invention.

It will be further appreciated, following known validation procedures of the PCA that are discussed elsewhere, a model can be established for a defined experiment such as the first experiment discussed above that has the defined experimental procedures and the data analysis procedures including the data presentation procedure. Therefore, following the known experimental and validation procedures a data base can be established, which includes a plurality of raw data and models for the respective various known analytes. After establishing the database, an unknown analyte can be predicted by comparing the PCA results of the unknown with the models of the respective known analytes in the database, wherein the comparison can be conducted with the known procedures, including visualization that is one of characteristics of the principal component analysis.

It will be additionally appreciated that, the present invention is not limited to only apply the PCA pattern recognition analysis and validation of the AC electrical properties of the respective analytes in fluids for establishing models to thereby predict unknowns. The present invention can apply any of the existing known analysis algorithms comprising multivariate analysis algorithms including the pattern recognition algorithms to classify and identify analytes in fluids, since those of ordinary skill in the art, who can compare strength with weakness of each algorithm, can choose one algorithm that is best for the particular interest of study. The additional analysis algorithms are known elsewhere (Beebe, K. R.; Pell, R. J.; Seasholtz, M. B.; Chemometrics: A Practical Guide, Wiley, New York 1998; J. of Chemometrics, John Wiley & Son, Ltd.), comprising SIMCA (Soft Independent Modeling of Class Analogy), KNN (K Nearest Neighbor), HCA (Hierarchical Cluster Analysis), CDA (Canonical Discriminant Analysis), CLS (Classical Least Squares), PCR (Principal Component Regression), PLS (Partial Least Squares Regression), supervised and unsupervised learning neural network and fuzzy neural network techniques.

The above illustrated experiments applies a signal preprocessing algorithm, which is disclosed in Equations [5-7]

of change of the electrical properties of the respective analytes at each swept frequency. Therefore, a matrix of the raw data set can be constructed for the further data analysis of the analyte identification. However, it will be appreciated that, in addition to this algorithm, other algorithms reported elsewhere also can be applied for the signal pre-processing.

Furthermore, it can be understood from the above experimental results that, instead of identifying analytes in fluids from application of the multiple frequency detection, the present invention can also be used to detect the presence of analytes of interest with a single frequency detection. For example, in GC analysis, mixed chemicals of an analyte are eluted separately out of the column by a carrier gas (usually hydrogen, or helium, or nitrogen). Each chemical can be detected in presence because of different AC electrical properties from the carrier gas and chemicals at the applied frequency, such as the impedance and its phase sensitive components. The above illustrated chemical separation process is also occurred in LC, wherein a solvent or a solvent mixture carries each chemical in an analyte of the chemical mixture out of a column. Therefore, the chemicals can be detected by applying one of the above disclosed electrical properties at a frequency.

In the application of the present invention from a preferred embodiment to design a GC detector, the first spatial electrode of the sensor in the single sensor configuration is a collar shaped hollow cylinder. The hollow cylindrical electrode is positioned at a top of a hollow jet connected to the end of the column, wherein the jet and hollow electrode are further positioned coaxially to the column end. The second spatial electrode of the sensor is a straight and thin member, which is positioned so as to be aligned with a rotation axis of the hollow cylindrical first electrode, either inside or outside of the cylindrical electrode. The GC detector from the present invention has a number of advantages, as compared with the existing GC detectors including the flame ionization detector (FID), thermal conductivity detector (TCD) and electron capture detector (ECD). The advantages include non-destructive, universal, simple for easy manufacturing and low cost.

Furthermore, for the above disclosed GC application of detecting presence of the chemicals using the impedance or current or voltage, the periodic electrical excitation signals of voltage or current can be applied to the GC detector of the present invention, which include the square, triangular and sawtooth wave forms of non-sinusoidal waves. This will simplify electrical circuits of the analyzing device.

The similar electrode structure is also appropriate for a new detector of the LC except the jet that must be electrically non-conductive.

As another example, detection of known flammable gases such as methane is critical for safe operation in the mine industry. Detection of such gases can also be achieved by using the sensor of the present invention, which is operated at a frequency by the excitation signals including the square, triangular and sawtooth wave forms to detect one electrical property.

Figure 7B:
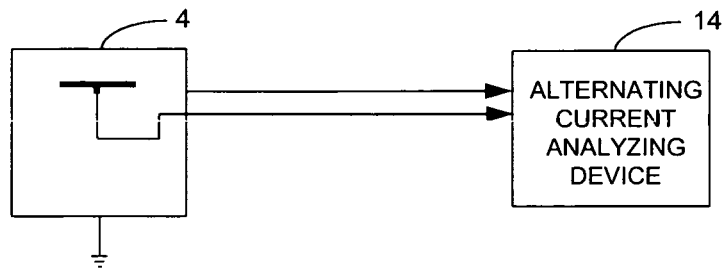
FIG. 7B shows a sidewall is properly grounded in connection of the sensor 4 to the alternating current analyzing device 9.

In addition, referring to FIGS. 7A and 7B there is illustrated a sensor according to the present invention, wherein the two electrodes may be formed in many ways. For example, when a first electrode is positioned at a location close to a sidewall of a container or other structure made of electrically conductive material which is electrically grounded, then the sidewall of the container or other structure may be served as a second electrode. The analyte in the fluid to be tested can be directed to pass through the gap between the first electrode and the sidewall of the container or other structure, which functions as the second electrode.

The present invention sensor operated by the periodic including AC electrical excitation signals with swept frequencies has many advantages. It utilizes an analytical sensor in the single sensor configuration from one measurement to generate spectra of the patterned electrical properties to record the analyte characteristics. The small size of the sensor which results in low power consumption on sensor temperature regulation and small volume requirement also allows the practical implementation of the dual sensor detection which, in addition to the analytical sensor, incorporates a reference sensor with the identical configurations. With this dual sensor detection, effects of background subjects can also be eliminated including humidity levels, aging effect of the polymer films and changes in testing including sensor responses induced by temperature variations.

The sensor of the single sensor configuration and method of the present invention also operate using swept frequencies including a preferred low frequency range between 10 KHz and 1 MHz. Application of the swept frequencies enables the application of the sensor having a small size to obtain the patterned electrical information of the analyte. The small sensor including a small sensor compartment determines a low power consumption to control temperature of the sensor compartment containing an analyte in a fluid, which is positioned between the sensor electrodes. It further allows the use of the temperature programming including the gradient and constant temperature programming to improve the detection and identification of the analyte in the fluid. In addition, applying the electric periodic excitation including the AC electrical excitation signals at the same amplitude, the present invention provides opportunities to use all types of adsorbent, absorbent and sorbent materials, including organic, inorganic, and metal materials. Combined with all of the above discussed advantages, it results in the present invention sensor instrument that is low in cost to produce, compact in size, portable, and easy to use.

The above disclosure introduces the core technology of the present invention sensor having two paired electrodes in the single sensor configuration operated by the periodic including the AC electrical excitation having varied including swept frequencies. However, as illustrated in the section of the prior art of this disclosure, there is still a room for improving the sensor from increasing the output of the sensor while reducing its physical size plus improving its electrical characteristics.

Referring to FIG. 8, there is illustrated preferred embodiment of a sensor 1' in the single sensor configuration having integrated electrodes, which is an improved embodiment according to the sensor 1. As illustrated, the sensor includes identical first, second and third metal conductors 5, 6 and 7 serving as the respective electrodes, which are positioned equally spaced apart, in order, alignment and parallel with each other. In addition, the first and third outer conductors 5 and 7 are the outer electrodes, and connected by a first lead wire serving as a first electrical pole 8 to be a group of the integrated electrodes. The second conductor 6, which is positioned at the middle of an air gap between the outer conductors, is electrically connected by a second lead wire serving as a second electrical pole 9. The electrodes of the sensor 1' are positioned onto a substrate 10, which can be air, or ceramics, or silicon to thereby be the respective integrated spatial electrodes, or thick film electrodes, or thin film electrodes. In addition, the above illustrated lead wires also can be printed onto the respective ceramic and silicon substrates. Therefore, the lead wires can be broadly defined as the electrically conducting means.

It will be appreciated that, regarding the electrical properties of the sensor 1', it is equivalent to those of two pairs of the sensor 1 if the paired electrodes 5 and 6 are the same as the paired electrodes of the sensor 1. Therefore, the sensor 1' has the same output as that of two sensor 1 connected in parallel. However, the sensor 1' only has three electrodes, as compared with four electrodes of the connected two sensors 1. The result is that the sensor 1' has smaller sizes as compared with the two parallel connected sensors 1. Therefore, the present invention sensor 1' having the integrated electrodes possesses properties of having the same output of the raw electrical information of a sample but smaller physical sizes, including one less electrode, as compared with two parallel connected sensors 1. These properties make the present invention sensor be advantageous in the sensor miniaturization, which is one of the key aspects of the sensor technologies.

Further Referring to FIG. 9, there is illustrated that the first and second electrical poles 8 and 9 of the sensor 1' are connected to the alternating current analyzing device 14 that applies an AC voltage to the electrodes. It will be appreciated that at a moment when a positive voltage is applied to the first electrical pole 8 and a negative voltage is applied to the second electrical pole 9, the outer electrodes 5 and 7 are positively charged and middle inner electrode 7 is negatively charged. Therefore, the two outer positively charged electrodes shield the negatively charged middle inner electrode, and the outermost electrical field of the sensor 1' is symmetrical relative to the middle electrode.

The same situation of shielding the middle electrode also exists when a positive voltage is applied to the middle electrode 6 and a negative voltage is applied to the outer electrodes 5 and 7. Therefore, the sensor 1' in the single configuration has its unique electrical properties, including the middle electrode 6 that is always shielded by the two outer electrodes 5 and 7, and its outermost electrical field that is symmetrical to the surrounding electromagnetical environment. These properties are critical to the present invention sensor and method that applies the AC electricity.

Referring to FIGS. 8A and 8B, there is illustrated dual sensor of the present invention, which utilizes two identical sensors 1', one serving as an analytical sensor 2' and the other as a reference sensor 3'. The dual sensor has two embodiments, an integrated one 13' and another separated one 12'.

It can be realized that the disclosed embodiment of the sensor 1' has the least number of the integrated electrodes as compared with allowable number of the integrated electrodes according to the spirit and scope of the present invention. Broadly speaking, a general embodiment of the sensor 1' could have a total of an odd number of the identical conductors serving as the respective electrodes, which are positioned equally spaced apart, in order, alignment and parallel with each other. Within the electrodes, the odd numbered conductors are connected in parallel by a first lead wire serving as a first electrical pole to thereby form a first group of the integrated electrodes. Two outermost electrodes and one middle electrode in the first group are served as the respective outermost electrodes and innermost electrode of the sensor. The even numbered electrodes are connected in parallel by a second lead wire serving as a second electrical pole to form a second group of the integrated electrodes.

Referring to FIG. 10, there is illustrated materials 11 that are positioned between the electrodes 5 and 6, and between the electrodes 7 and 6. It will be appreciated that all the aspects are the same as those of the above disclosed application of the materials 11 to the sensor 1. The aspects include the purpose to apply the materials 11, and procedures to apply the materials including the surface treatment of the substrate 10 if it is the ceramics or silicon, in addition to the solid supports positioned between air gaps of the respective two adjacent electrodes. Therefore, for reducing length of this disclosure, these same aspects will not be repeated.

Figure 11:
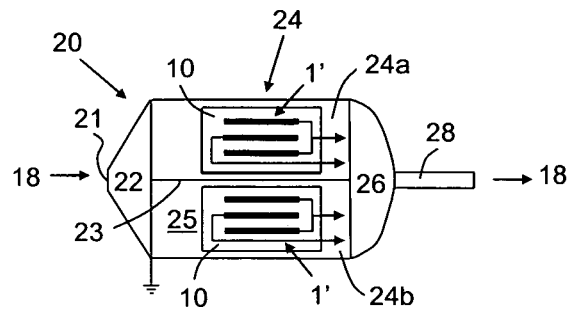
FIG. 11 shows a schematic diagram in a top view of a sensor compartment, wherein a top of a middle section of the sensor compartment is removed so that two sensors are seen that are positioned in the respective two subchambers.
Figure 12:
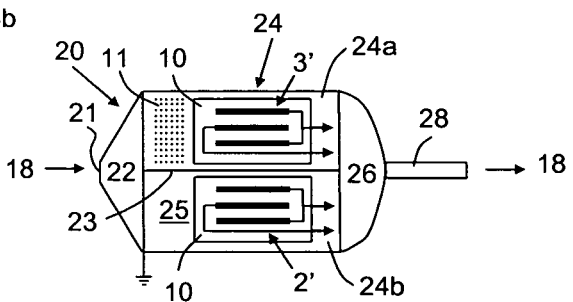
FIG. 12 shows the same structural configuration of the sensor compartment in FIG. 11, in addition to show that adsorbent materials 11 are positioned at the front of one of the subchambers to adsorb the analyte in fluid, so that only the fluid can pass between the sensor electrodes positioned inside of the subchamber.
Figure 13:
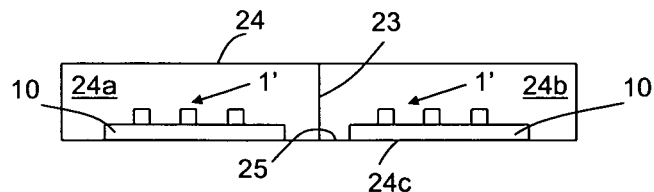
FIG. 13 shows a transverse cross sectional view of the middle section of the sensor compartment as illustrated in FIG. 11.

FIGS. 11 to 13 illustrate application of a hollow sensor compartment 20 to position two identical sensors 1'. The sensor compartment 20 is made of metals such as copper or metal alloys such as copper alloys for shielding electromagnetic radiation, when the compartment is electrically grounded.

The hollow sensor compartment 20 which has a limit thickness is comprised of the front section 22 having an inlet 21 connected to a middle section 24, which is further connected to a rear section 26 that links an outlet 28, such as a pipe. In this setting, a sample 18 of an analyte in a fluid in the exterior environment adjacent the compartment 20 will be driven to enter into the inlet 21, and then finally exit from the outlet 28 of the sensor compartment 20.

The front section 22 of the sensor compartment has a shape of an isosceles triangle, including a wide transverse closed rear side that is connected to a front side of the middle rectangular section 24 of the sensor compartment 20. It will be appreciated that, when it enters into the front section 22, the sample 18 will gradually reduce a flow speed due to a wide and gradually increased transverse width of the front section 22, as compared with a narrow interior size of the inlet 21. In this situation in addition to the limited thickness of the sensor compartment 20, a laminar flow can be achieved when the sample flows through the sensor compartment 20. The arcuate or round rear section 26 of the sensor compartment will reduce formation of a turbulent flow of the sample, which also contributes to achieve the laminar flow of the sample. It will be appreciated that the laminar flow creates a uniform distribution of the sample to the sensor integrated electrodes.

Referring to FIGS. 11 to 13 again, the interior of the middle section 24 of the sensor compartment 20 is divided by a middle upward wall 23 positioned in parallel with the flow direction, which forms first and second identical subchambers 24a and 24b. Within each subchamber, there is positioned one identical sensor 1' having three electrodes, which are aligned with the flow direction. However, it will be appreciated that the electrodes of each identical sensor 1' can also be positioned at any angle to the flow direction including the angle of 90 degrees. Referring to the figures, it will be appreciated that, the electrical poles are connected to the alternating current analyzing device 14.

As illustrated above, the electrodes of the sensor 1' in the single sensor configuration can have the air substrate to be the spatial electrodes, or the respective ceramic or silicon substrates to be the respective thick and thin film electrodes. Referring to FIGS. 11 to 13, in the case when the sensor 1' has either thick or thin film electrodes, the respective ceramic substrate 10 or silicon substrate 10 is adhered to the interior side 25 of the bottom 24c of the middle section 24 of the sensor compartment. It will be appreciated that both ceramic, silicon and metal materials are good heat conductors. Therefore, if a heater is attached to the exterior side of the bottom 24c, wherein heating of the heater is controlled according to the temperature programming, it can easily control the temperature of the sensor compartment 20, including the inside positioned each sensor 1' having the electrodes and flowing sample 18 of the analyte in the fluid. In addition, the small size of the each sensor 1' only requires a small volume of the subchamber, which results in a low power consumption for the temperature control of the sensor compartment 20.

The metallic sensor compartment 20 when it is electrically grounded shields the electromagnetic radiation emitted by the first sensor 1' which is applied by the AC electrical swept frequencies. Similarly, electromagnetic radiation emitted by the second sensor 1' is also shielded. Therefore, application of the sensor compartment can prevent influence from a possible cross talk of the electromagnetic radiation emitted by the first and second sensors 1'.

It will be appreciated that, by providing an example of two sensors 1' connected to the device 14, the above illustration discloses one embodiment of the present invention, which employs at least two sensors to detect and identify analytes in fluids. Implementation of the embodiment follows the spirit and scope of the present invention, finding dimensions that describe characteristics of the analytes in the fluids.

In this embodiment, referring to FIG. 11, it will be appreciated that, there is an option for the adsorbent materials 11 to be positioned between the paired electrodes of one of the at least two sensor. During testing analytes in fluids, each analyte in a fluid is tested by each of the at least two sensors according to a testing procedure. The sensor filled with the adsorbent materials will record the AC related electrical properties including resistance and reactance as the detectable information for an adsorbed chemical or adsorbed chemicals from the analyte in the fluid, when the adsorption process is completed.

Obviously, in a situation if each of the analytes is a chemical mixture, dimensions of the respective resistance and reactance from the sensor filled with the adsorbent materials represent the characteristics of adsorbed chemical or chemicals that are a part of the chemical mixture. They are different from dimensions of the resistance and reactance from the sensor without the filled adsorbent materials, which represent an overall characteristics of all different chemicals in the analyte. In another situation if each of the analytes is different chemical, the resulting electrical properties from the sensor filled with the adsorbent materials will have a high signal-to-noise ratio for each analyte, as compared with those from the sensor without the filled adsorbent materials. The resulting high signal-to-nose ratio is still positive for the analyte detection and identification. Therefore, having the spirit and scope of finding the characteristic dimensions of analytes in measurement, the present invention can conduct better detection and identification of analytes in fluids with implementation of the strategy having at least two sensors when it is needed.

Following the above analogy, another one option of the present invention is that each of the at least two sensor 1' is filled with different adsorbent materials. In this setting, each of the at least two sensors 1' records the same analyte at the different dimensions. Therefore, application of the at least two sensors 1' provide more resolving power for identifying the analyte.

Referring to FIG. 12, there is illustrated another embodiment for applying the dural sensor, wherein one sensor 1', positioned in the subchamber 24b is served as the analytical sensor 2', and the other positioned in the subchamber 24a is served as the reference sensor 3'. The sensors can include electrodes in the forms of spatial, thick film and thin film electrodes with or without the filled adsorbent materials 11. However, the same adsorbent materials 11 are positioned at the front of the subchamber 24a for trapping chemical or chemicals of interest, so that only those that are not the interest of the study, which pass through the adsorbent materials 11, can continually pass among the integrated electrodes of the reference sensor 3'.

As disclosed before, after combining the electrical properties of the respective analytical and reference sensors 2' and 3', there remains only electrical properties of the chemical or chemicals of the interest including those which are served as the biochemical marker or markers. This is an effective way to detect known chemical or chemicals including biochemical marker or markers of an analyte for the analyte identification with respect to the medical diagnoses of diseases.

It will be appreciated that, in addition to the embodiment of the integrated dual sensor 13' shown in FIG. 12, the analytical and reference sensors 2' and 3' have the respective independent sensor compartments if they are in the separated form 12'.

As disclosed before, because of its small size, simple structure and low cost, the sensor in the single sensor configuration of the present invention is practically suitable for the disposable sensor configuration. In design of the disposable sensors, for example, which are positioned inside of the respective sensor subchambers 24a and 24b, the front section 22 of the sensor compartment 20 can be designed to be detachable. This means that the front section 22 can be press-fit to connect to the middle section 24 of the sensor compartment. The disposable sensor including the spatial, thick and thin film electrodes also can be in the same press-fit manner for their respective first and second electrical poles to contact the respective metal sockets covered with appropriate electrical insulation materials, wherein the sockets are positioned inside of the respective subchambers 24a and 24b, and connected to the device 14. Following this concept, a detailed design is obvious for those of ordinary skill in the art, therefore the present invention can have the disposable sensors, which is one unique feature of the present invention.

The AC analyzing device 14 is comprised of a component of electronic circuits to generate AC excitation signals having varied including swept frequencies. The excitation signals can be applied to the sensor 1 or 1' containing a sample of an analyte in a fluid to obtain the sample electrical properties, wherein the properties can be measured by another electronic component of the device.

The device 14 can be manufactured according to a number of electronic structures that are well known. It can be configured following the electronic configuration of the Agilent 4294A comprising a digital control, source, transducer, and vector ratio detector, wherein the source provides all analog signals of the AC excitation voltage having swept frequencies and variable voltage magnitudes that are applied to the sample, the transducer comprises a transform of the measured sample impedance into two AC signal voltages, the vector ratio detector comprises conversion of two AC voltages into digital data, and the digital control comprises digital data processing for outputting results of the sample measurement.

The device 14 can also be designed from electronic circuits based on the analog Lock-in principle, interfaced by including ADC, which is further connected to the digital section for data acquisition (Princeton Applied Research, Oak Ridge, Tenn. USA). In addition, the digital analogy of the Lock-in principle, which is the digital correlation, can be additionally applied (Solartron, Farboroagh, Hampshire UK).

It will be appreciated that the above disclosed techniques apply AC signals with swept frequencies comprising a sinusoidal wave that sequentially varies frequencies to excite an analyte as a measurement time elapses, wherein there is only one frequency at any point of time when the analyte is excited. Instead of such one-frequency excitation mechanism, a polyfrequency excitation mechanism is also appropriate to construct the detection module 14 (Zahner-Elektrik Gmbh & CokG, Kronach Germany), which applies a plurality of sinusoidal waves having the respective different frequencies to excite an analyte at any point of time. Such excitation could further employ the Fourier transform techniques.

Besides the above disclosed electronic configurations of the respective commercial instruments, the device 14 also can be assembled in application of including an integrated circuit chip AD5933 (Analog Devices, MA USA). The chip is operated according to the mechanism of discrete Fourier transform (DFT), which generates real and imaginary data of an impedance at each of frequencies.

As disclosed before, if it is only for one frequency detection, the periodic excitation signal is adequate for the device 14, comprising the square, triangular and sawtooth wave forms of the non-sinusoidal waves. Regarding electrical circuits for generating a single frequency of an AC voltage or current, the following are well known: RC phase-shift oscillator, Wien-bridge oscillator, Colpitts oscillator, Hartley oscillator, and square-wave generator (Aminian, Ali.; Kazimierczuk, Marian; Electronic Devices, a design approach, Pearson Prentice Hall 2004).

Examples (II)

The following are examples and experimental information of the present invention, regarding the sensor having the integrated electrodes in the single sensor configuration operated by an AC voltage of a single frequency to test samples of lubricating oil, which are offered by way of illustration only and not by way of limitation and restriction.

A sensor was constructed with three identical plates of a copper alloy serving as the respective electrodes. Each metal plate had a thickness of approximately 1 mm and the shape of a table tennis bat, including a bottom rectangular section connected to a top longitudinal bar having a top end serving as the top end of the plate, wherein the bar is aligned with a longitudinal central line of the rectangular section. The rectangular section had a width of 15 mm and a length of 30 mm, and a bottom hole positioned adjacent to the bottom transverse side of the width and on the central line. The bar had a length 20 mm, and a top hole positioned at 15 mm to the top end. In addition, there was a mark on the bar which was adjacent to the top transverse side of the width of the rectangular section.

The three plates are positioned upwardly in parallel and in alignment with each other to be the respective left, middle and right plates. Two Nylon washers were positioned between left and middle plates, and aligned with the respective bottom and top holes. Similarly, two additional Nylon washers were positioned between middle and right plates, and aligned with the respective bottom and top holes. Each washer had a thickness of approximately 1.5 mm and was served as a spacer. In addition, top and bottom Nylon screws were used to penetrate through the respective washers and top and bottom holes of the respective three plates, and were then fastened by the respective two Nylon nuts. Therefore, the sensor had the same fixed air gap between two adjacent plates. The top ends of the respective left and right plates were electrically connected by a wire serving as a first electrical pole, and the top end of the middle plate was electrically connected by another wire serving as a second electrical pole.

An AC analyzing device was assembled by application of including an IC chip AB-112 of Wien Bridge Oscillator (Analog Devices, MA USA). After adjustment of electrical parameters, the chip output an AC voltage having 5.40 volts of the root mean square (rms) values at 7.25 kHz, which was measured by a Radio Shack digital multimeter (Cat. No.: 22-168A) and verified by an oscilloscope.

Two oil samples were used. The first one was a new oil, and second one was an used oil which was spent for 5000 miles. The following was a procedure to prepare the oil samples. Multiple quarts of commercial oil were purchased and then mixed together to be a pool of the homogeneous oil. A small volume of the homogeneous oil was collected, which was served as the sample of the new oil without contamination. Approximately five quarts of the homogeneous oil were poured into the lubricating oil system of a passage car. After the car ran 5000 mils, the oil was collected, and a small portion was used as the sample of the used oil having contaminates serving as analytes according to concepts of the present invention.

A testing circuit was constructed, which was a voltage divider including the sensor connected to a reference impedance of 10 M ohm. Within the circuit, the first electrical pole was connected to the output terminal of the IC chip, and second electrical pole was connected to a first lead of the reference impedance having a second lead that was electrically grounded.

The measurement was conducted by using the multimeter to measure voltages in the rms value across the respective sensor and reference impedance. Therefore, impedance of the sensor was calculated according to the measured voltages.

The testing procedures in order were for measuring the blank electrodes, electrodes filled with the new oil, and electrodes filled with the used oil. When measuring the respective new and used oil, the bottom rectangular section of the sensor was immersed into the respective oil samples, wherein top levels of the respective oil samples were reached to the mark of the sensor. In addition, before testing the sample of the used oil, the electrodes were first washed with the same used oil. Application of these two steps was to minimize the experiment errors.

Test results showed an impedance of 31.0 M Ohm for the blank electrodes of the sensor which was filled with air, 24.8 M Ohm for the sensor filled with the new oil, and 23.9 M Ohm for the used oil. The testing results were consistent with theories of the higher the dielectric constant of a medium between the electrodes of a sensor, the lower the impedance of the sensor having the corresponding medium. It will be appreciated that, comparing values of the dielectric constants of the respective media in the test, air of the blank electrodes has the lowest value, new oil the lower value, and the used oil the highest value that was caused in the presence of the contaminates serving as the analytes, wherein the contaminates were produced in the usage of the oil.

It will be appreciated that, the results of the above disclosed experiment demonstrate that the present invention sensor 1' can be used to detect analytes in fluids when applying a single frequency of an AC voltage. It will be further appreciated that, the present invention sensor 1' can also be used to identify analytes in fluids when applying multiple frequencies of an AC voltage. This conclusion is based on the testing results of the EXAMPLES (I) and (II) in addition to the rationalization that the improved sensor 1' with the integrated electrodes has better electrical properties of the bigger output and more balanced electrical characteristics, as compared with the sensor 1 having the conventional two electrodes.

Of course the present invention is not intended to be restricted to any particular form or arrangement, or any specific embodiment, or any specific use, disclosed herein, since the same may be modified in various particulars or relations without departing from the spirit or scope of the claimed invention hereinabove shown and described of which the apparatus or method shown is intended only for illustration and disclosure of an operative embodiment and not to show all of the various forms or modifications in which this invention might be embodied or operated.

The present invention has been described in considerable detail in order to comply with the patent laws by providing full public disclosure of at least one of its forms. However, such detailed description is not intended in any way to limit the broad features or principles of the present invention. Although the above invention is described in some detail by way of illustration and example for purposes of clarity of understanding, it is apparent to those of ordinary skill in the art in light of the teaching of this invention that many changes and modifications may be made thereto without departing from the scope of the appended claims.

What is claimed is:

1. A sensor, comprising:
   a. an analytical sensor including first, second and third identical electrodes, which are positioned equally spaced apart in order, alignment and parallel with each other, wherein said first and third electrodes are electrically connected in parallel by a first electrically conducting means serving as a first electrical pole and said second electrode is connected by a second electrically conducting means serving as a second electrical pole, said first and second electrodes are electrically separated by a first non-conductive material and said second and third electrode are electrically separated by a second non-conductive material that is identical to said first non-conductive material;
   b. said analytical sensor is brought into contact with a first fluid containing an analyte;
   c. said first and second electrical poles of said analytical sensor are electrically connected to an alternating current (AC) analyzing device, wherein said AC analyzing device applies various frequencies of AC signals to said analytical sensor;
   d. AC related electrical properties are detected for said analytical sensor when contacted by said first fluid containing said analyte according to said applied various frequencies of said AC signals, wherein said electrical properties are detected at each of said applied various frequencies; and
   e. said detected AC related electrical properties according to a selected subgroup of said applied various frequencies are used for identification of said analyte.

2. The sensor as claimed in claim 1, wherein said AC related electrical properties include impedance, resistance, reactance, phase angle, voltage and current.

3. The sensor as claimed in claim 1, further comprising a first conductive material that is positioned between said first and second electrodes of said analytical sensor, and a second conductive material that is positioned between said second and third electrodes, wherein said first and second conductive materials are identical.

4. The sensor as claimed in claim 1, wherein said non-conductive material positioned between said electrodes is selected from the group consisting of polymer, polymer inorganic material composite, molecular sieves, particles of the respective silica gel, alumina, porous carbon, calcium carbonate and fluorocarbon, liquid organic salts, composite of one of platinum group of metals composited by filler consisting of inorganic or organic materials, polymer modified porous ceramic particles, polymer modified fluorocarbon particles, polymer modified porous silica, and polymer modified porous glass beads.

5. The sensor as claimed in claim 4, further comprising said electrodes of said analytical sensor that are spatial electrodes, or thick film electrodes having a ceramic substrate, or thin film electrodes having a silicon substrate, wherein surface treatment reagents are used to treat surfaces of the respective ceramic substrate, silicon substrate, and particles of the respective silica gel, alumina, porous carbon and fluorocarbon.

6. The sensor as claimed in claim 1, said analytical sensor further includes a total of an odd number of the identical conductors serving as the respective electrodes that are positioned equally spaced apart, in order, alignment and parallel with each other, wherein odd numbered electrodes from said total electrodes are connected in parallel by a first electrically conducting means serving as a first electrical pole to form a first group of integrated electrodes, and odd number electrodes are connected in parallel by a second electrically conducting means serving as a second electrical pole to form a second group of integrated electrodes.

7. The sensor as claimed in claim 1, further comprising means for implementing a temperature programming technique to said analytical sensor.

8. The sensor as claimed in claim 1, further comprising:
   a. said analytical sensor is brought into contact with a second fluid which is identical to said first fluid but does not contain any analyte;
   b. AC related electrical properties are detected for said analytical sensor when contacted by said second fluid according to said applied various frequencies of said AC signals, wherein said electrical properties are detected at each of said applied various frequencies;
   c. combined AC related electrical properties of said analyte are obtained by combining the respective AC related electrical properties of said analytical sensor when contacted by said first fluid containing said analyte with the respective AC related electrical properties of said analytical sensor when contacted by said second fluid, and
   d. said combined AC related electrical properties according to a selected subgroup of said applied various frequencies are used for identification of said analyte.

9. The sensor as claimed in claim 1, further comprising an odorant as said analyte.

10. The sensor as claimed in claim 1, wherein said analyte is selected from studies of materials containing illegal substances, environment concerns, medical interests including hospital concerns, scientific and research interests including space research interests, interests of industrial sectors including food, beverages, agricultural, chemical, petroleum, plastic, construction, pharmaceutical automobile, biochemical, and transportation, consumer interests including perfume, cosmetic, wine and flavor, and safety concerns including explosive, arson and road spill investigation.

11. The sensor as claimed in claim 1, further comprising a reference sensor that is identical to said analytical sensor, wherein said reference sensor is used for correcting background subjects and selectively detecting known biochemical marker or biochemical markers.

12. The sensor as claimed in claim 1, further comprising at least two of said analytical sensor.

13. A sensor, comprising:
   a. an analytical sensor including first, second and third identical electrodes, which are positioned equally spaced apart in order, alignment and parallel with each other, wherein said first and third electrodes are electrically connected in parallel by a first conducting means serving as a first electrical pole and said second electrode is connected by a second conducting means serving as a second electrical pole, said first and second electrodes are electrically separated by a first non-conductive material and said second and third electrode electrically separated by a second non-conductive material that is identical to said first non-conductive material;

b. said analytical sensor is brought into contact with a first fluid containing an analyte;
c. said first and second electrical poles of said analytical sensor are electrically connected to an alternating current (AC) analyzing device, wherein said AC analyzing device applies a frequency of an AC signal to said analytical sensor;
d. AC related electrical properties are detected for said analytical sensor when contacted by said first fluid containing said analyte according to said applied frequency of said AC signal; and
e. one of said detected AC related electrical properties is used for detection of said analyte.

14. The sensor as claimed in claim 13, wherein said AC related electrical properties include impedance, resistance, reactance, and phase angle.

15. The sensor as claimed in claim 13, wherein said non-conductive material positioned between said electrodes is selected from the group consisting of polymer, polymer inorganic material composite, molecular sieves, particles of the respective silica gel, alumina, porous carbon, calcium carbonate and fluorocarbon, liquid organic salts, composite of one of platinum group of metals composited by filler consisting of inorganic or organic materials, polymer modified porous ceramic particles, polymer modified fluorocarbon particles, polymer modified porous silica, and polymer modified porous glass beads.

16. The sensor as claimed in claim 13, further comprising a first conductive material that is positioned between said first and second electrodes of said analytical sensor, and a second conductive material that is positioned between said second and third electrodes, wherein said first and second conductive materials are identical.

17. The system as claimed in claim 13, wherein said analyte is selected from studies of materials containing illegal substances, environment concerns, medical interests including hospital concerns, scientific and research interests including space research interests, interests of industrial sectors including food, beverages, agricultural, chemical, petroleum, plastic, construction, pharmaceutical automobile, biochemical, and transportation, consumer interests including perfume, cosmetic, wine and flavor, and safety concerns including explosive, arson and road spill investigation.

18. The sensor as claimed in claim 13, further comprising said electrodes of said analytical sensor that are spatial electrodes, or thick film electrodes having a ceramic substrate, or thin film electrodes having a silicon substrate, wherein surface treatment reagents are used to treat surfaces of the respective ceramic substrate, silicon substrate, and particles of the respective silica gel, alumina, porous carbon and fluorocarbon.

19. The sensor as claimed in claim 18, said analytical sensor further includes a total of an odd number of the identical conductors serving as the respective electrodes that are positioned equally spaced apart, in order, alignment and parallel with each other, wherein odd numbered electrodes from said total electrodes are connected in parallel by a first electrically conducing means serving as a first electrical pole to form a first group of integrated electrodes, and even number electrodes are connected in parallel by a second conducting means serving as a second electrical pole to form a second group of integrated electrodes.

20. A sensor, comprising:
a. an analytical sensor comprising first, second and third identical electrodes, which are positioned equally spaced apart in order, alignment and parallel with each other, wherein said first and third electrodes are electrically connected in parallel by a first electrically conducting means serving as a first electrical pole and said second electrode is connected by a second electrically conducting means serving as a second electrical pole, said first and second electrodes are electrically separated by a first non-conductive material and said second and third electrode are electrically separated by a second non-conductive material that is identical to said first non-conductive material;
b. said analytical sensor is brought into contact with a fluid containing an analyte;
c. means, applied by various frequencies of AC signals, for detecting AC related electrical properties of said analytical sensor when contacted by said fluid containing said analyte according to said applied various frequencies, wherein said electrical properties are detected at each of said applied various frequencies; and
d. said detected AC related electrical properties according to a selected subgroup of said applied various frequencies are used for identification of said analyte.

* * * * *